US012613528B2

(12) United States Patent
Kreitinger et al.

(10) Patent No.: US 12,613,528 B2
(45) Date of Patent: Apr. 28, 2026

(54) APPARATUSES, SYSTEMS, AND METHODS FOR GAS FLUX MEASUREMENTS WITH MOBILE PLATFORMS

(71) Applicant: Bridger Photonics, Inc., Bozeman, MT (US)

(72) Inventors: Aaron Thomas Kreitinger, Bozeman, MT (US); Michael James Thorpe, Bozeman, MT (US); Peter Aaron Roos, Bozeman, MT (US)

(73) Assignee: Bridger Photonics, Inc., Bozeman, MT (US)

( * ) Notice: Subject to any disclaimer, the term of this patent is extended or adjusted under 35 U.S.C. 154(b) by 0 days.

(21) Appl. No.: 18/582,001

(22) Filed: Feb. 20, 2024

(65) Prior Publication Data

US 2024/0210950 A1 Jun. 27, 2024

Related U.S. Application Data

(63) Continuation of application No. 17/419,708, filed as application No. PCT/US2020/013737 on Jan. 15, 2020, now Pat. No. 11,940,817.

(Continued)

(51) Int. Cl.
*G05D 1/00* (2024.01)
*B64D 45/00* (2006.01)
(Continued)

(52) U.S. Cl.
CPC ............. *G05D 1/104* (2013.01); *B64D 45/00* (2013.01); *B64U 10/13* (2023.01);
(Continued)

(58) Field of Classification Search
None
See application file for complete search history.

(56) References Cited

U.S. PATENT DOCUMENTS

| | | |
|---|---|---|
| 4,135,092 A | 1/1979 | Milly |
| 9,488,978 B2 | 11/2016 | Callou et al. |

(Continued)

FOREIGN PATENT DOCUMENTS

| | | | | |
|---|---|---|---|---|
| EP | 2975597 A1 * | 1/2016 | ............. | G01W 1/08 |
| JP | 2016050813 A | 4/2016 | | |

(Continued)

OTHER PUBLICATIONS

[Published as 2022-0082495] U.S. Appl. No. 17/419,708, titled "Apparatuses, Systems, and Methods for Gas Flux Measurements With Mobile Platforms" filed Jun. 29, 2021.

(Continued)

*Primary Examiner* — Peter D Nolan
*Assistant Examiner* — Michael F Whalen
(74) *Attorney, Agent, or Firm* — Dorsey & Whitney LLP

(57) ABSTRACT

Apparatuses, systems, and methods for open path laser spectroscopy with mobile platforms. An example system may include a first mobile platform and a second mobile platform, each of which supports a payload. A light beam directed from one payload to another may define a measurement path, which may be at a particular height above the ground. The payloads may determine a gas concentration along the measurement path. Wind information at the measurement height may be used to determine a gas flux. One or both of the mobile platforms may then move to a new location, and take a measurement along a new measurement path. By combining the measurement paths, gas flux through a flux surface may be determined.

18 Claims, 12 Drawing Sheets

Related U.S. Application Data

(60) Provisional application No. 62/792,767, filed on Jan. 15, 2019.

(51) Int. Cl.

| | |
|---|---|
| *B64U 10/13* | (2023.01) |
| *G01N 33/00* | (2006.01) |
| *G01S 17/95* | (2006.01) |
| *G01S 19/43* | (2010.01) |
| *G05D 1/695* | (2024.01) |
| *B64U 101/35* | (2023.01) |
| *G01N 21/17* | (2006.01) |
| *G01N 21/31* | (2006.01) |

(52) U.S. Cl.

CPC .......... *G01N 33/0027* (2013.01); *G01S 17/95* (2013.01); *G01S 19/43* (2013.01); *G05D 1/695* (2024.01); *B64U 2101/35* (2023.01); *B64U 2201/102* (2023.01); *B64U 2201/20* (2023.01); *G01N 2021/1795* (2013.01); *G01N 21/31* (2013.01)

(56) References Cited

U.S. PATENT DOCUMENTS

| | | | |
|---|---|---|---|
| 10,060,942 | B2 | 8/2018 | Burba et al. |
| 10,094,773 | B2 | 10/2018 | Myshak et al. |
| 11,940,817 | B2 | 3/2024 | Kreitinger et al. |
| 2010/0049382 | A1* | 2/2010 | Akalinli .................. G01W 1/02 701/16 |

| | | | |
|---|---|---|---|
| 2011/0122397 | A1* | 5/2011 | Wong ...................... G01S 17/95 356/438 |
| 2012/0092649 | A1* | 4/2012 | Wong ...................... G01W 1/00 356/72 |
| 2017/0088261 | A1 | 3/2017 | Sequeira et al. |
| 2019/0147753 | A1* | 5/2019 | Hendrian ................. G08G 5/34 701/14 |
| 2019/0234868 | A1 | 8/2019 | Tanomura et al. |
| 2022/0082495 | A1 | 3/2022 | Kreitinger et al. |

FOREIGN PATENT DOCUMENTS

| | | | |
|---|---|---|---|
| JP | 2017110984 A * | 6/2017 | |
| WO | 2018008675 A1 | 1/2018 | |
| WO | 2020150388 A1 | 7/2020 | |

OTHER PUBLICATIONS

Extended European Search Report dated Sep. 16, 2022 for European Patent Application No. 20741032.5.

International Search Report and Written Opinion for PCT Application No. PCT/US2020/013737, mailed Apr. 1, 2020.

PCT Application No. PCT/US20/13737 titled "Apparatuses, Systems, and Methods for Gas Flux Measurements With Mobile Platforms" filed Jan. 15, 2020.

Examination Report for European Patent Application No. 20741032. 5-1206 dated Mar. 21, 2025, pp. all.

Office Action for Canadian Patent Application No. 3123634 dated Jan. 15, 2025, pp. all.

* cited by examiner

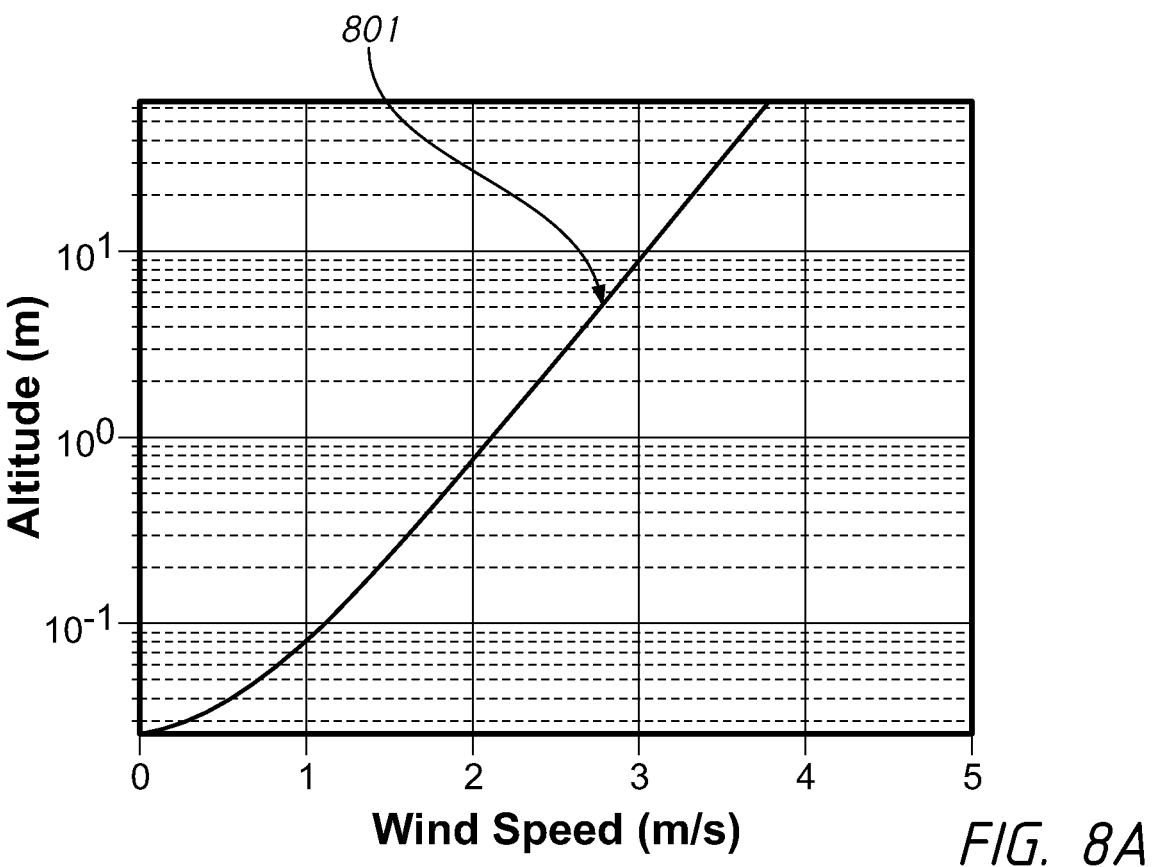
Wind Speed (m/s)
*FIG. 8A*
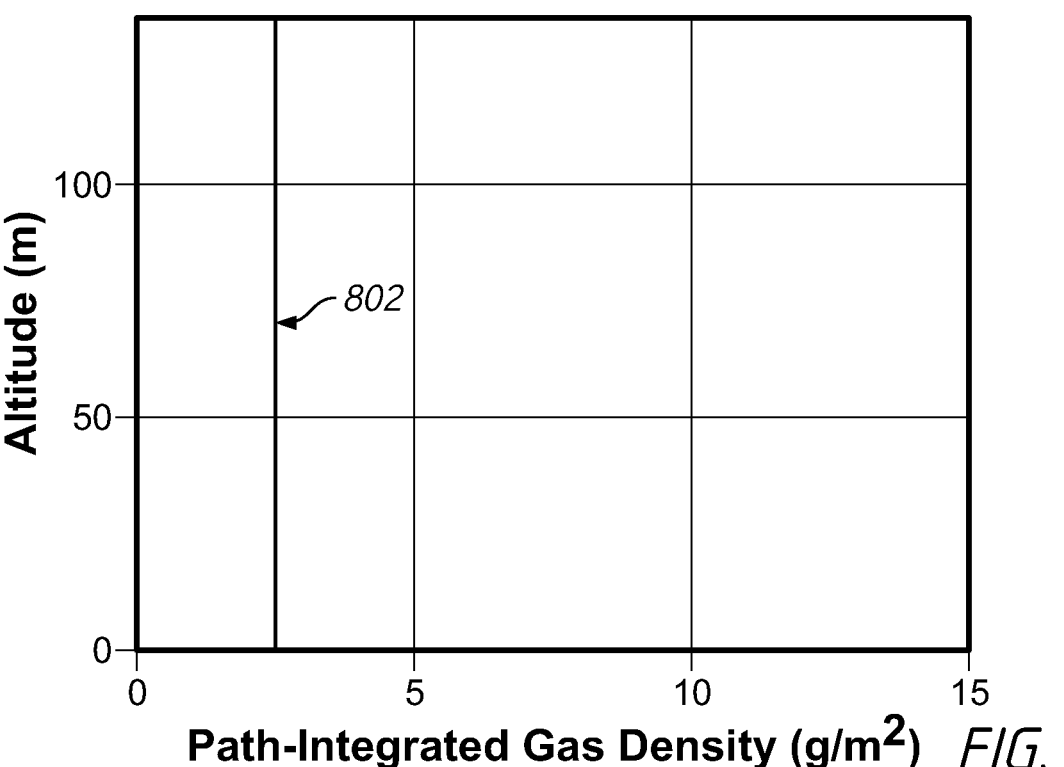
Path-Integrated Gas Density (g/m²) *FIG. 8B*

803

Log Wind Profile:

$$u(z) = u_0 \ln\left(\frac{z-z_d}{z_0}\right)$$

$u_0$ = 0.4 m/s, $z_d$ = 0.02 m, $z_0$ = 0.005 m

Wind Speed (m/s)

Altitude (m)

804

Path-Integrated Gas Density (g/m$^2$)

Altitude (m)

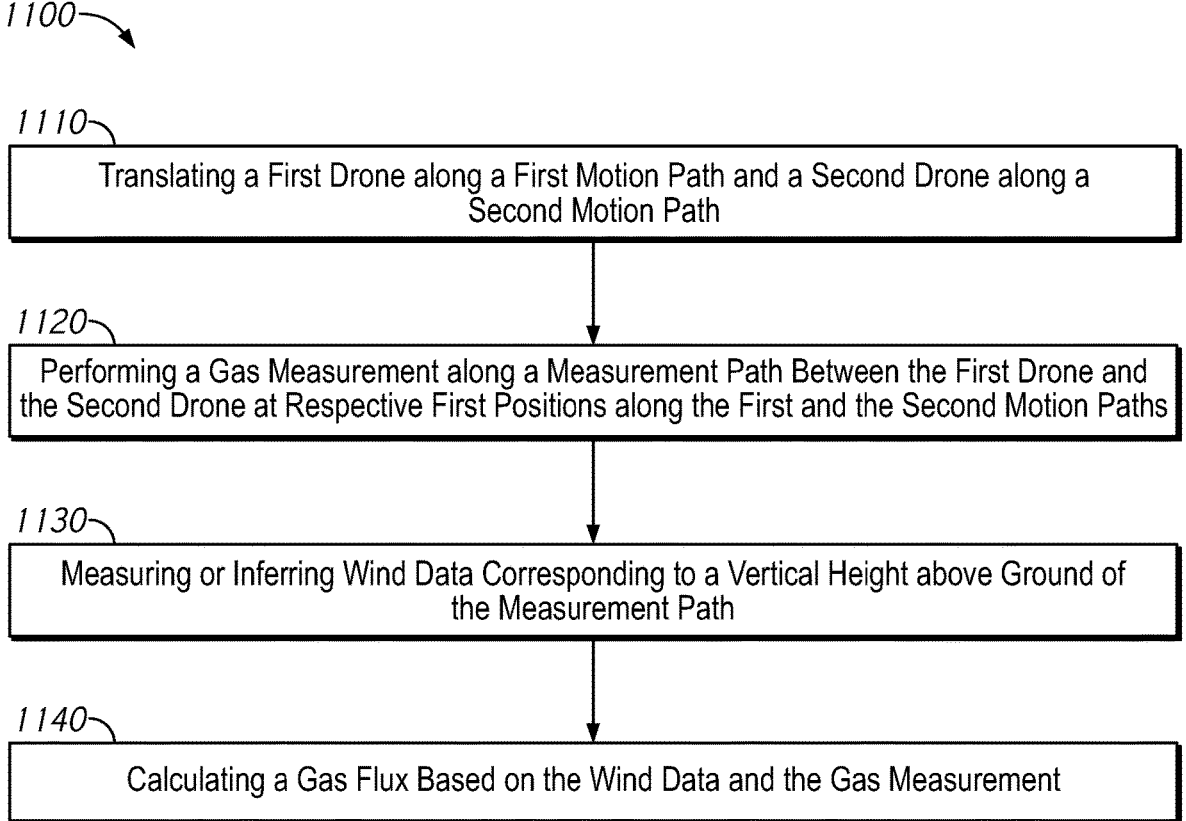

1100

1110
Translating a First Drone along a First Motion Path and a Second Drone along a Second Motion Path 1120
Performing a Gas Measurement along a Measurement Path Between the First Drone and the Second Drone at Respective First Positions along the First and the Second Motion Paths 1130
Measuring or Inferring Wind Data Corresponding to a Vertical Height above Ground of the Measurement Path 1140
Calculating a Gas Flux Based on the Wind Data and the Gas Measurement

FIG. 11

APPARATUSES, SYSTEMS, AND METHODS FOR GAS FLUX MEASUREMENTS WITH MOBILE PLATFORMS

CROSS-REFERENCE TO RELATED APPLICATION(S)

This application is a continuation of U.S. patent application Ser. No. 17/419,708, filed Jun. 29, 2021, which is a 371 national phase application of PCT Application No. PCT/US2020/013737, filed Jan. 15, 2020, which claims the benefit under 35 U.S.C. § 119 of the earlier filing date of U.S. Provisional Application Ser. No. 62/792,767 filed Jan. 15, 2019, the entire contents of which are hereby incorporated by reference in their entirety for any purpose.

TECHNICAL FIELD

Embodiments of the invention relate generally to gas flux measurements, and particularly, to open-path laser spectroscopy.

BACKGROUND

There may be a variety of applications where it is useful to measure a gas flux. The gas flux may be a measure of the rate flow of the gas through a particular surface, which may be arbitrarily defined. The gas of interest may be present in an environment which includes other gases. For example, the gas may be emitted into the atmosphere.

Sensors may be used for gas flux and emission rate quantification and monitoring. Cost effective technologies and methods that can perform accurate gas flux quantification may be desirable to allow classification and prioritization of individual leaks for repair, mitigation, or remediation, and may also enable total emissions estimates for sites or regions to determine an aggregate gas emissions.

SUMMARY

In at least one aspect, the present disclosure relates to a system which includes a first drone, a second drone, a laser, a receiver, and wind measurement device and a processor. The first drone follows a first motion path and the second drone follows a second motion path. The laser produces a transmitted laser beam directed from the first drone toward the second drone. The transmitted laser beam is used to perform a gas measurement. The receiver receives at least a portion of the transmitted laser beam that is used to perform the gas measurement. The wind measurement device produces wind data. The processor calculates a gas flux based at least in part on the gas measurement and the wind data.

The second drone may house the receiver. The second drone may be equipped with a reflector which may reflect the transmitted laser beam back to the first drone, and the first drone may be equipped with the receiver which may receive the transmitted laser beam. The wind measurement device may be mounted on one of the first drone or the second drone. The wind measurement device may produce the wind data based, at least in part, on attitude information of the first drone or the second drone. The first motion path and the second motion path may be coordinated such that the first drone and the second drone move in similar vertical directions at the same time.

The gas measurement may be an integrated-path gas concentration measurement. A plurality of integrated-path gas concentration measurements may be performed to generate a vertical gas concentration profile. A plurality of wind data points may be measured or inferred to generate a vertical wind profile. The calculation of the gas flux is based, at least in part, on the vertical gas concentration profile and the vertical wind profile.

In at least one aspect, the present disclosure relates to a method. The method includes translating a first drone along a first motion path and a second drone along a second motion path. The method includes performing a gas measurement along a measurement path between the first drone and the second drone at respective first positions along the first and the second motion paths. The method includes measuring or inferring wind data associated with a vertical height above ground of the measurement path. The method includes calculating a gas flux along the measurement path based on the wind data and the gas measurement.

The gas measurement may be an integrated-path gas concentration measurement. The first and second drone motion paths may be coordinated such that the measurement path is approximately parallel to a ground surface. The wind measurement may be performed by the first drone the second drone, or combinations thereof.

The method may also include performing a plurality of gas measurements, each associated with one of a plurality of measurement paths based on a position of the first drone along the first motion path and the second drone along the second motion path. The method may also include measuring or inferring the wind data at a plurality of vertical heights above the ground, each associated with a height of one of the plurality of measurement paths.

Calculating the gas flux may be based at least in part on a vertical gas concentration distribution and a vertical wind profile. The method may also include determining a total gas flux based, at least in part, by a first gas flux associated with a first flux surface and a second gas flux associated with a second flux surface. The first gas flux may be associated with the first flux surface which is downwind of an emission source and the second gas flux may be associated with the second flux surface which is upwind of the emission source.

In at least one aspect, the present disclosure relates to a system. The system includes a first mobile platform at a first position, a transmitter, a wind measurement device, and a processor. The transmitter directs a laser beam along a first measurement path between the first mobile platform and a second mobile platform at a respective first position. The wind measurement device determines wind data at a height of the first measurement path. The processor determines a gas concentration along the first measurement path and determines a first gas flux through the first measurement path based on the gas concentration and the wind data at the first measurement path.

The first platform and the second platform may travel to respective second positions. The transmitter may direct a laser beam along a second measurement path and the wind measurement device may determine wind data at a height of the second measurement path. The processor may determine a gas concentration along the second measurement path and may determine a second gas flux through the second measurement path based on the gas concentration and the wind data at the second measurement path. The processor may also determine a flux through a flux surface based on the first gas flux and the second gas flux.

The first mobile platform and the second mobile platform may be drones. The wind measurement device may include a sensor mounted on the first mobile platform or the second mobile platform. The wind measurement device may determine the wind data based in part on attitude information of the first mobile platform or the second mobile platform.

The first mobile platform may vary the first position. The first measurement path may include measurements at a variety of angles between the first mobile platform and the second mobile platform. The processor may generate a tomographic reconstruction of the gas concentration based, at least in part, on the measurements at the variety of angles.

BRIEF DESCRIPTION OF THE DRAWINGS

FIG. 8A-8D are a set of graphs showing wind speed and gas density profiles for flux surfaces upwind and downwind of an area of interest according to some embodiments of the present disclosure.

FIG. 11 is a flow chart depicting a method according to some embodiments of the present disclosure.

DETAILED DESCRIPTION

Figure 1:
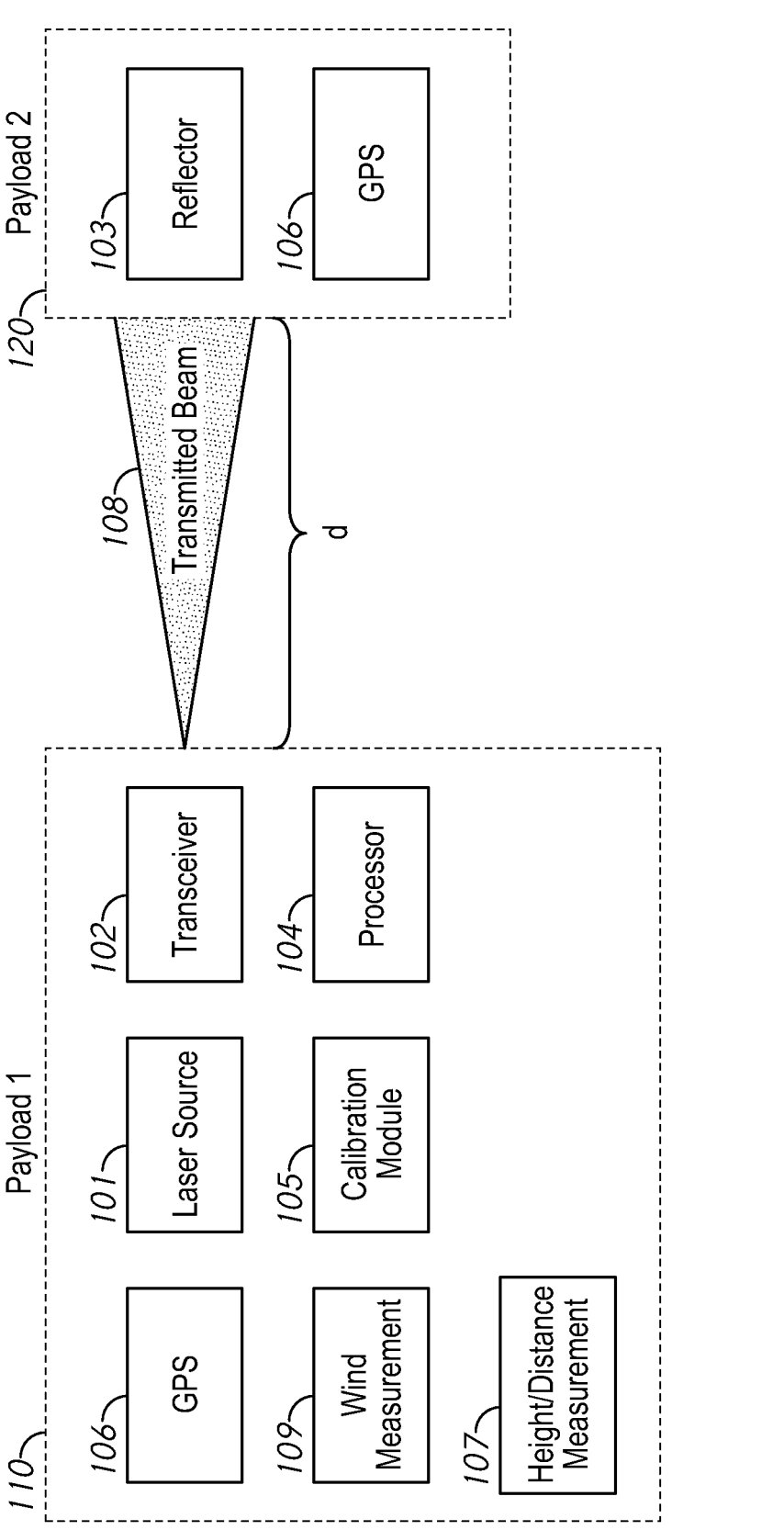
FIG. 1 is a block diagram of a first payload and a second payload according to embodiments of the present disclosure.

The following description of certain embodiments is merely exemplary in nature and is in no way intended to limit the scope of the disclosure or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the disclosure. Moreover, for the purpose of clarity, detailed descriptions of certain features will not be discussed when they would be apparent to those with skill in the art so as not to obscure the description of embodiments of the disclosure. The following detailed description is therefore not to be taken in a limiting sense, and the scope of the disclosure is defined only by the appended claims.

Gas flux may be determined using various methods. Spectroscopy may be useful for determining the concentration of a target gas. A laser beam (or other light source) may travel from a transmitter a distance through an environment (e.g., the atmosphere) which contains (or is suspected to contain) a target gas to a receiver. Based on known properties of the interaction of the target gas with light, a concentration of the gas may be determined along a measurement path (e.g., along the laser beam). The gas concentration may include a path-integrated gas concentration measurement. There may be many scenarios where it is possible to assume that lateral movement of the gas across the measurement path is primarily due to bulk flow of gasses in the environment (e.g., wind). Information about the wind may be combined with the gas concentration to determine a flux density across the measurement path. Combining one or more flux density measurements with incremental height information may give a gas flux through a surface including the measurement path(s). However, one or both of the gas measurement and the wind data may be spatially dependent. Accurate gas flux measurements may therefore improve with knowledge of a wind data corresponding to a gas concentration for a given spatial location. To determine gas flux corresponding to a gas plume with large spatial extent such that the wind data (e.g. wind speed or direction) changes appreciably across the plume, multiple gas measurements, corresponding to multiple wind data points may be desired.

A dominant or important spatial dependence of wind or gas concentration may be in the vertical dimension relative to the ground. It may therefore be advantageous to determine a vertical wind profile and/or a vertical dependence of a gas measurement. A vertical wind profile may refer to the dependence of a wind characteristic (e.g. speed and/or direction) with vertical height from the ground. It may thus be useful to build both a vertical wind profile and a vertical profile of the gas concentration in order to determine overall flux.

Embodiments of the present disclosure are drawn to gas flux measurements with mobile platforms. A system for determining gas flux may include a first mobile platform which follows a first (generally vertical) path and a second mobile platform which follows a second (generally vertical) path. While the paths may generally be vertical, other directions are also possible. The first mobile platform may have a first payload which includes a transmitter (e.g., a laser source) which provides light along a path between the drones. The second mobile platform may have a second payload which includes a receiver (and/or a reflector which returns the light to a receiver on the first mobile platform). Based on changes in the light along the path between the transmitter and receiver, a gas concentration along the measurement path may be determined. Wind data, which may include wind speed, may be determined at the elevation of the measurement path. For example, one or more of the mobile platforms may measure the wind speed at their current elevation, using, for example, a sensor, such as one or more anemometer, mounted on the mobile platform. The gas concentration information and the wind speed information may both be dependent, in part, on the height at which the measurement(s) were obtained. One or more of the mobile platforms may measure a height of one or more mobile platforms, using, for example, one or more altimeters, or by any other means. Since the mobile platforms are mobile, the position of the drones may be changed, and the process may be repeated. Multiple such flux measurements may be used to build a total gas flux measurement.

Figure 10:
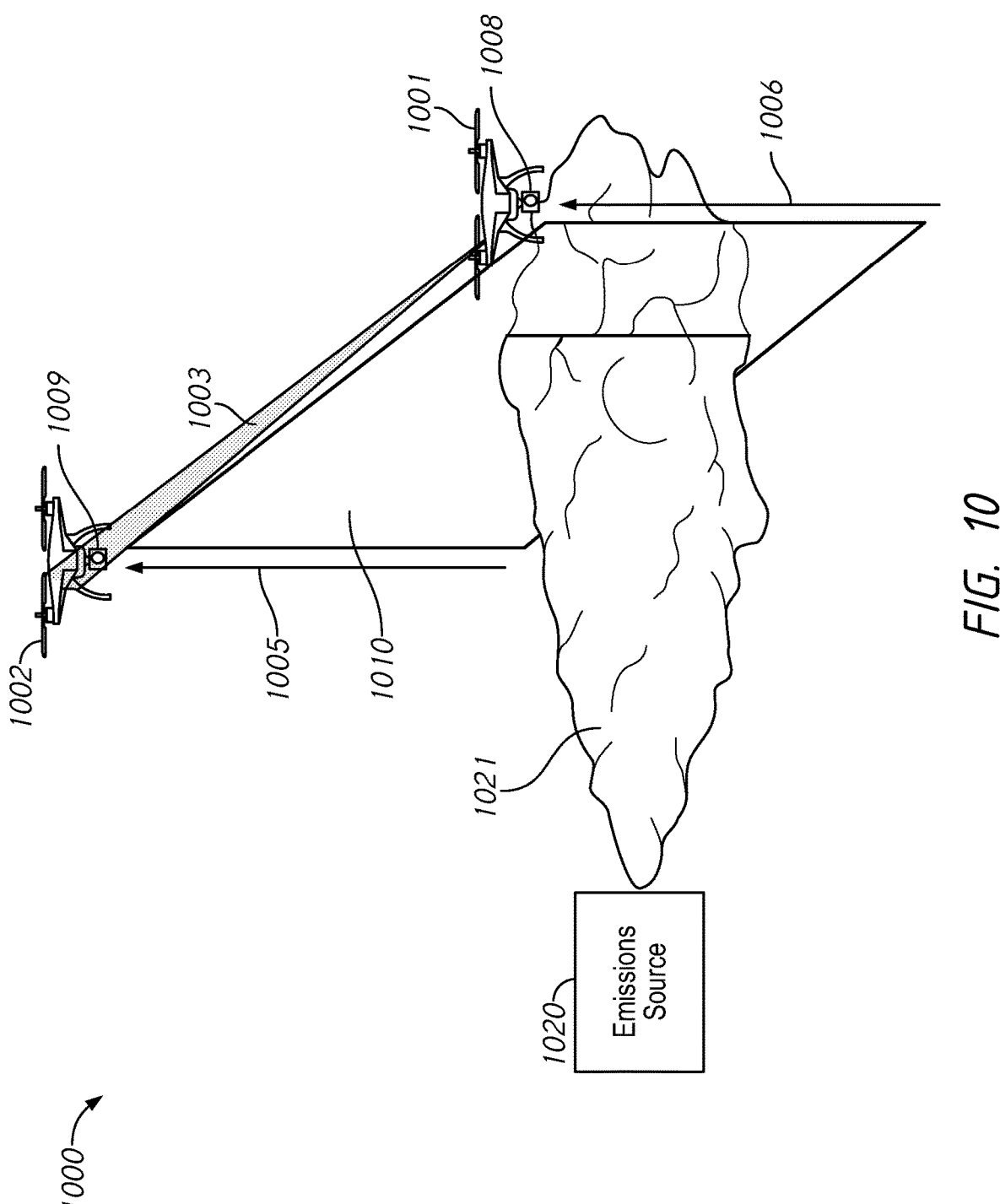
FIG. 10 is a block diagram of an optical system according to embodiments of the present disclosure.

FIG. 10 is a block diagram of an optical system according to embodiments of the present disclosure. The optical system 1000 includes a first mobile platform 1001 and a second mobile platform 1002. The two mobile platforms 1001 and

1002 may be useful for measuring the flux of a target gas 1021 through a surface 1010, which may be defined in part by the travel paths 1005 and 1006 of the first mobile platform and the second mobile platform 1001 and 1002.

The optical system 1000 may be an environment which includes an emissions source 1020. The emissions source 1020 may emit a target gas 1021 into the environment. The target gas 1021 may be a gas which is not normally present in the environment or may represent a cloud of gas at a different concentration than would be normally found in the environment. The target gas 1021 may extend as a plume away from the emissions source 1020. In many example environments, airflow, such as wind, may be present, and the target gas 1021 may be a plume which generally extends away from the emission source 1020.

The emissions source 1020 may be a natural or artificial source. For example, the emissions source 1020 may be an industrial site such as an oil well or manufacturing plant, a natural formation such as an oil field or a volcano, a municipal site such as a wastewater treatment facility or landfill, or any other site which is known or suspected of releasing the target gas 1021. The target gas 1021 may be a gas which is of interest in research, environmental monitoring, safety, regulation or combinations thereof. In some embodiments, the target gas 1021 may be a greenhouse gas, such as $CO_2$ or methane. In some embodiments, the emission source 1020 may be a site which produces a particular gas 1021, and the plume may represent a leak of that gas into the environment.

A system which includes a first mobile platform 1001 and a second mobile platform 1002 may be used to characterize the target gas 1021 by measuring its flux through one or more flux surfaces 1010. The mobile platforms 1001 and 1002 may be any platform capable of movement while carrying the payloads 1008 and 1009. For example, the mobile platforms 1001 and 1002 may be aerial vehicles capable of motion in three dimensions relative to the ground. In some embodiments, the mobile platforms 1001 and 1002 may be unmanned aerial systems (UASs or drones). In some embodiments, the mobile platforms 1001 and 1002 may be rotary wing aerial vehicles such as a helicopter or multi-rotor vehicle (e.g., a quadcopter). While the term 'drone' may generally be used herein to describe various embodiments, it should be understood that other types of mobile platform could be used in addition to, or instead of drones.

The mobile platforms 1001 and 1002 may receive (and/or contain) instructions which cause them to perform a measurement operation. In some embodiments the mobile platforms 1001 and 1002 may include one or more computer readable mediums (e.g., memory) which may store executable instructions, as well as one or more processors (e.g., processor 104) which may execute the instructions to perform one or more measurements. In this manner, processing circuitry and/or software may be used to implement measurements described herein. The processor 104 may be implemented, for example, using one or more central processing unit(s) (CPUs), graphics processing unit(s) (GPUs), controllers, microcontrollers, and/or circuitry such as application specific integrated circuits (ASICs) and/or field programmable gate arrays (FPGAs). Additional electronics may also be included in mobile platforms described herein, including, but not limited to, one or more filters, digital-to-analog converters, analog-to-digital converters, transform blocks, etc. In some embodiments, the mobile platforms 1001 and 1002 may be coupled (e.g., through wireless signals) to a controller or base station which provides instructions for performing one or more measurements. In some embodiments, one of the mobile platforms 1001 and 1002 may act as a controller for the other mobile platform 1001 and 1002. In some embodiments, a mix of techniques (e.g., onboard instructions, received instructions, communication between platforms) may be used.

As part of performing the measurement, the two mobile platforms 1001 and 1002 may travel to an initial location. At the initial location, each of the mobile platforms 1001 and 1002 may be a height above the ground. The initial location may define an initial measurement path 1003 between the payloads 1008 and 1009 of the mobile platforms 1001 and 1002. The initial measurement path, and subsequent measurement paths, may be characterized in part by their heights. For example, for an ith measurement the first mobile platform 1001 may have a first height $z1(i)$ and the second mobile platform 1002 may have a second height $22(i)$. The measurement path may have a height $zm(i)$, which is based on the first and the second heights (e.g., $zm(z1(i), z2(i))$). In some embodiments, the first height and the second height may be the same for each measurement and the measurement height may be equal to this height (e.g., $zm(i)=z1(i)=z2(i)$). In some embodiments, the two heights may be different (e.g., $z1(i) \neq z2(i)$). In some embodiments, the heights may be the same for some measurements and different for other measurements. In some embodiments where the heights are different, the measurement height may be treated as an average of the two heights. In some embodiments, the height of the measurement path may be determined, at least in part, based on the characteristics of the travel paths 1005 and 1006. In some embodiments the height may be determined, at least in part, based on one or more measurements by one or both of the mobile platforms 1001 and 1002. For example, the platforms 1001/1002 may include one or more global positioning system (GPS), inertial measurement unit (IMU), altimeter, and/or range finders which may determine an elevation or a height of the platform(s).

The measurement path 1003 may represent an optical path between the payloads 1008 and 1009. The first payload 1008 and/or the second payload 1009 may include optics which measure a gas concentration along the measurement path 1003. For example, the first payload 1008 may provide light (e.g., a laser beam) along the measurement path 1003 and the second payload 1009 may include a reflector, such as a retroreflector, which returns the light back along the measurement path 1003 to a receiver in the first payload 1008. The receiver may measure an intensity of the received light. Based on the measured intensity of the received light, the intensity of the provided light and optical factors such as the length of the measurement path 1003, and the extinction coefficient of the target gas 1021 at the wavelength of the light, a gas concentration along the measurement path 1003 may be calculated.

To determine a flux, information about the motion of the gas across the measurement path 1003 may be needed. If the measurement path 1003 is sufficiently far from the emission source 1020, wind may dominate the motion of the target gas 1021. Accordingly, wind data, such as wind speed and direction may be combined with the gas concentration to determine a flux density across the measurement path 1003. The wind data may be obtained from measurement by a remote sensor, measurement by one or more of the mobile platforms 1001 and 1002, calculation, weather database information, or combinations thereof. The flux density may be converted to a flux by multiplying the flux density by an incremental height (e.g., $\Delta z$). In some embodiments, the incremental height $\Delta z$ may represent an arbitrary unit of vertical spacing assigned to each measurement path 1003. In some embodiments, $\Delta z$ may represent a vertical spacing between measurement paths 1003, which may be based on characteristics (e.g., beam divergence) of the transmitted beam and/or characteristics of the travel paths 1005/1006. The flux(es) through one or more measurement beams may be used to determine a total flux through the flux surface 1010.

The wind speed and/or direction may be expressed at vertical increments, may be expressed continuously as a function of vertical height from the ground, or combinations thereof. In some embodiments, a vertical wind profile may be determined from a wind measurement (e.g. wind speed and/or direction) at one or more vertical heights above the ground. Wind data at other heights above the ground may be inferred or calculated based on the measured wind data using known or estimated dependences of wind as a function of vertical height above the ground. The dependence of wind speed and/or direction as a function of vertical height above the ground may depend on various factors such as ground roughness, vegetation, obstructions, or combinations thereof.

To obtain wind speed and direction estimates at the location of the gas concentration measurements, wind data may be acquired in the vicinity of locations where flux estimates are being performed by positioning one or several sensors, such as anemometer(s), at known height(s) above ground, near the measurement locations. In measurement scenarios with significant topographic variability it may be useful to combine anemometer measurements performed at one or more locations with topographic data, 3D elevation models, and/or surface roughness estimates to determine the vertical wind speed and direction profiles at relevant locations using fluid dynamics simulations.

In some embodiments, it may therefore be advantageous to place wind speed measuring devices and/or wind direction measuring devices (one or more wind measurement devices) on or with the mobile platforms 1001 and/or 1002. Any of a variety of sensors may be used to determine wind speed and/or wind direction. For example, compact pitot probe, cup and vane, sonic, ultrasonic, acoustic resonance, wind LiDAR, and/or other sensors are available that are compatible with mounting on the mobile platforms 1001 and 1002. Such a mobile-platform-mounted wind measurement device may, in some embodiments, offer full 360° air speed and/or direction measurements. Such embodiments may allow for the direct measurement of spatial (e.g. vertical) wind profiles. The sensors may have the added benefit of aiding station-keeping, hovering, and/or dynamic positioning control in gusty and turbulent environments.

Instead of, or in addition to, a direct wind-measurement device (e.g., a sensor), it is also possible to use the flight characteristics and/or dynamic positioning control of one or more of the mobile platforms 1001 and 1002 to estimate wind speed. It is possible to estimate the wind speed and/or direction using, for example, the attitude information (e.g. pitch, roll, and/or yaw) of the mobile platform 1001/1002. In some embodiments, a mobile platform used for a wind measurement may be the same or different from the mobile platforms 1001/1002 used for a gas measurement. Any number of mobile platforms, or combination of mobile and fixed platforms, may be used for wind measurements and for gas measurements. Any method or instrument may be used to determine or estimate wind speed and/or direction. Measurements from multiple wind measurements (fixed, mobile, or inferred) may be combined or weighted in any way to determine a wind profile.

In some embodiments, when local wind measurements are either unavailable or insufficient, or to augment local wind data, wind speed and direction data may also be accessed via, or interpolated from, observations recorded at nearby weather stations. This data may be available for download from a number of online services such as the National Climatic Data Center operated by NOAA, MesoWest operated by the University of Utah and Weather Underground. Weather station wind speed and direction data may generally be recorded at a height of 10 m above ground and may provide reliable wind speed and direction information in cases where flux estimates are performed near an automatically archived weather station. Finally, weather modeling services such as Meteoblue may use weather station observations and topography data as inputs to high-spatial-resolution weather models to provide wind data at any location on the planet effectively interpolating, or filling in the gaps, between weather station locations.

After taking the initial measurement, one or more of the mobile platforms 1001/1002 may move to a next position. This, in turn, may change a location of the measurement path 1003. In some embodiments, one or more of the mobile platforms 1001/1002 may move along a flight path 1005/1006, respectively, which has a vertical component. In some embodiments, the mobile platforms 1001 and 1002 may move along flight paths 1005 and 1006 which are primarily vertical. Once the mobile platforms 101 and 1002 have each reached their next positions, a gas concentration (and/or wind measurement) may be taken at the new position of the measurement path 1003. A flux density (and/or flux) along the new measurement path may then be calculated. In some embodiments, the movement of the mobile platforms 1001 and 1002 may be continuous, and the payloads 1008 and 1009 may collect measurements as the mobile platforms 1001 and 1002 are in motion.

In some embodiments, the mobile platforms 1001/1002 may have coordinated flight paths 1005 and 1006 which may be useful for acquiring concentration measurements that may enable tomographic reconstruction of multi-dimensional gas concentration distributions, which in turn may allow for determination of the gas concentration as a function of both horizontal and vertical positions relative to the ground.

By taking multiple measurements along multiple measurement paths, a total flux of the target gas 1021 through a flux surface 1010 may be determined. The total flux across the flux surface 1010 may be based on the flux density (and/or flux) across some number of measurement paths 1003 which are part of the flux surface 1010. In some embodiments, fluxes may be calculated for each measurement path and summed or otherwise combined to find a total flux through the surface. In some embodiments, the flux densities at each measurement path may be used and the total flux through the surface 1010 may be found by integrating along the height of the surface 1010. Since both mobile platforms 1001 and 1002 may be independently mobile, it may be possible to carry out measurements though flux surfaces 1010 of arbitrary location, orientation and/or shape.

Since each of the measurement paths 1003 which make up a flux surface 1010 may be associated with a measurement height, the wind data at the height of that measurement path 1003 may be used to calculate the flux density (and/or flux) through that measurement path 1003. Since wind data may vary strongly as a function of height, obtaining the wind data as a function of height may be advantageous for increasing the accuracy of the measurements through the overall flux surface 1010, and may aid in allowing for greater flexibility in selecting flux surfaces 1010. An average of multiple vertical wind measurements may also be used to calculate a flux. The average of multiple vertical wind measurements may be combined with an average of multiple gas concentration measurements to calculate a flux.

In some embodiments, flux(es) or total flux(es) may be determined for multiple flux surfaces 1010. For example, the mobile platforms 1001 and 1002 may reposition and perform a set of measurements for a second flux surface. In some embodiments, additional mobile platforms may be used to measure additional flux surfaces. In some embodiments, two of the plurality of flux surfaces may be a flux surface upwind and/or a flux surface downwind of the emission source 1020. The gas flux determinations from the plurality of flux surfaces may be combined (e.g. vector summed or subtracted) to produce accurate estimates of gas 1021 emission rates.

The total gas flux associated with one or more flux surfaces 1010 in the vicinity of an emission source 1020 may be analyzed to determine the emission rate associated with a particular emission source. One or more actions may be taken based on the measured emission rate. For example, regulatory action, repair or upgrade of the emissions source, levying of fines, remediation of the environmental source, changing an operation of the emission source, performing a research study, or combinations thereof. For example, the emission source 1020 may be an oilfield. Mobile platforms may collect flux information about the oilfield to determine a rate at which a greenhouse gas, such as methane, is being emitted. Based on the determined methane emission rate, one or more remediations (e.g., plugging a leak, reducing drilling operations, etc.) may be performed.

FIG. 1 is a block diagram of a first payload and a second payload according to embodiments of the present disclosure. The first payload 110 may, in some embodiments be included in the first payload 1008 of FIG. 10 and the second payload may, in some embodiments, be included in the second payload 1009 of FIG. 10. The block diagrams of FIG. 1 may represent simplified representations of the payloads 1008 and 1009, and fewer or additional components may be included in other embodiments. In some embodiments, the payloads 1008 and 1009 may be drone payloads which may be attached to drones. For example, in some embodiments, the payloads 110 and 120 may be packaged in a housing with a standard shape and/or mounting equipment for attachment to a drone. In some embodiments, the payloads 110 and 120 may be integral to the drones. The first payload 110 includes a laser source 101, a transceiver (transmitter and receiver) 102, processor 104, a calibration module 105, a GPS receiver 106, a height/distance measurement device 107, and a wind measurement device 109. The second payload 120 includes a retro-reflector 103 and a GPS receiver 106.

An example embodiment illustrating an open-path laser spectroscopy system for performing a gas measurement (e.g. path-integrated gas concentration) of a target gas species (e.g., target gas 1021 of FIG. 10) along the path (e.g., along transmitted beam 108) between two drones undergoing coordinated flight is shown in FIG. 1. The open-path laser spectroscopy system includes at least one laser source 101 for producing an open-path laser spectroscopy signal and a transceiver 102 for transmitting the laser spectroscopy beam from the first payload 110 to the second payload 120 (e.g., from a first mobile platform to a second mobile platform). The system may also comprise a retro-reflector 103 as part of the second payload 120 to reflect a portion of the transmitted beam back to receiver 102 mounted on the first payload 110. Additionally, the system may comprise processor 104 (e.g., a processor) for computing a path-integrated gas concentration measurement from the received open-path laser spectroscopy signal. The system may also comprise a gimbal or beam scanner for directing the transmitted beam and a calibration module 105, which may comprise a gas cell containing a sample of the target gas species, for laser frequency stabilization and calibration of the concentration measurement. The height/distance measurement device 107 may determine a height of the mobile platform (and/or height of the measurement path) and/or a distance between the payloads 110 and 120. The wind measurement device 109 may determine wind data at the location of the payload 110. In some embodiments, components such as the processor 104, height/distance measurement device 107 and wind measurement device 109 may also be present in the second payload 120.

The measurement system may include a GPS receiver 106 mounted on one or both payloads 110/120 to measure the position of each drone during coordinated flight. In some embodiments the two payloads may be outfitted with RTK GPS receivers, and a fixed position base station may be used to achieve increased accuracy of the drones' position during coordinated flight. The drone separation may be selected such that the wind profile in the horizontal direction does not change appreciably between the drones. The drone separation may be determined using GPS or any ranging method such as laser ranging.

The open-path laser spectroscopy concentration measurement method may vary depending on several factors, such as the desired drone separation and/or the target gas species being measured, and may include, but is not limited to, tunable diode laser absorption spectroscopy (TDLAS), wavelength modulation spectroscopy (WMS), differential absorption lidar (DIAL), chirped laser dispersion spectroscopy (CLaDS), Dual-comb spectroscopy (DCS) and others.

The laser source 101 may produce laser light at a wavelength associated with a target gas. For example, the laser light may be at a peak wavelength of an extinction coefficient of the target gas. Other relationships between the laser light and target gas may be used in other examples. The laser light may be modulated in frequency, wavelength, intensity, phase, polarization, or any other characteristic. In some embodiments, laser source 101 may be a broadband source and one or more optics (e.g., filters) may be used to change the wavelength of the light. The transceiver 102 may include optics which may direct the light from the source 101 into the transmitted beam 108.

The transmitted beam 108 may be directed towards the second payload 120. In some embodiments, position data (e.g., data from the GPS receiver 106 of the first and/or second payloads 110/120) or measurements of received laser light intensity performed on the second payload, may be used (e.g. in a feedback loop) to direct the transmitted beam 108 towards the second payload 120. In the embodiment of FIG. 1, the second payload 120 includes a reflector 103. The reflector 103 may return all or a portion of the received beam 108 back to the transceiver 102. In some embodiments, the reflector 103 may reflect substantially all of the transmitted beam 108 back to the transceiver. In some embodiments, the reflector 103 may be a retro-reflector.

The transceiver 102 may receive the beam 108 from the reflector 103. The transceiver 102 may measure (or redirect to a detector which may measure) one or more properties of the received light. The light may have travelled a distance (e.g., 2d) from the transceiver 102 to the reflector 103 and back to the transceiver 102. While traveling the distance, the light may interact with the target gas. For example, the target gas may reflect, scatter, and/or absorb the light. A processor 104 may compare the transmitted light to the received light to determine the concentration of the target gas along the measurement path (e.g., along the transmitted beam 108). For example, the intensities of the transmitted and received light may be compared. In some embodiments, calibration data from the calibration module 105 may be used, in part, to determine the concentration of the target gas.

The height/distance measurement device 107 may be used to find a height of the mobile platform carrying the payload 110 and/or a distance between the payloads 110 and 120. For example, the height/distance measurement device 107 may include an altimeter which may measure a height of the payload 110. In some embodiments, the height/distance measurement device 107 may include a range finder (e.g., a laser or ultrasonic range finder) which may measure a distance to a surface. The range finder may, for example, measure a distance to the ground and/or a distance to the payload 120. The distance between the payloads 110 and 120 may be used by the processor 104 to determine a gas concentration. The distance to the ground may be used to determine a height of the payload 110. In some embodiments, the GPS 106 may also be used to determine the altitude, or other positional coordinate of the payload 110.

The wind measurement device 109 may be used to collect wind data at the location of the payload 110. For example, the wind measurement device 109 may include a wind sensor, such as an anemometer, which is mounted (e.g., on an outer surface) of the payload 110. The wind measurement device 109 may collect data such as wind speed and/or direction at the location of the payload 110. The processor 104 may use the wind data along with the gas measurement to determine a flux density and/or flux along the measurement path (e.g., along the transmitted beam 108).

Figure 2:
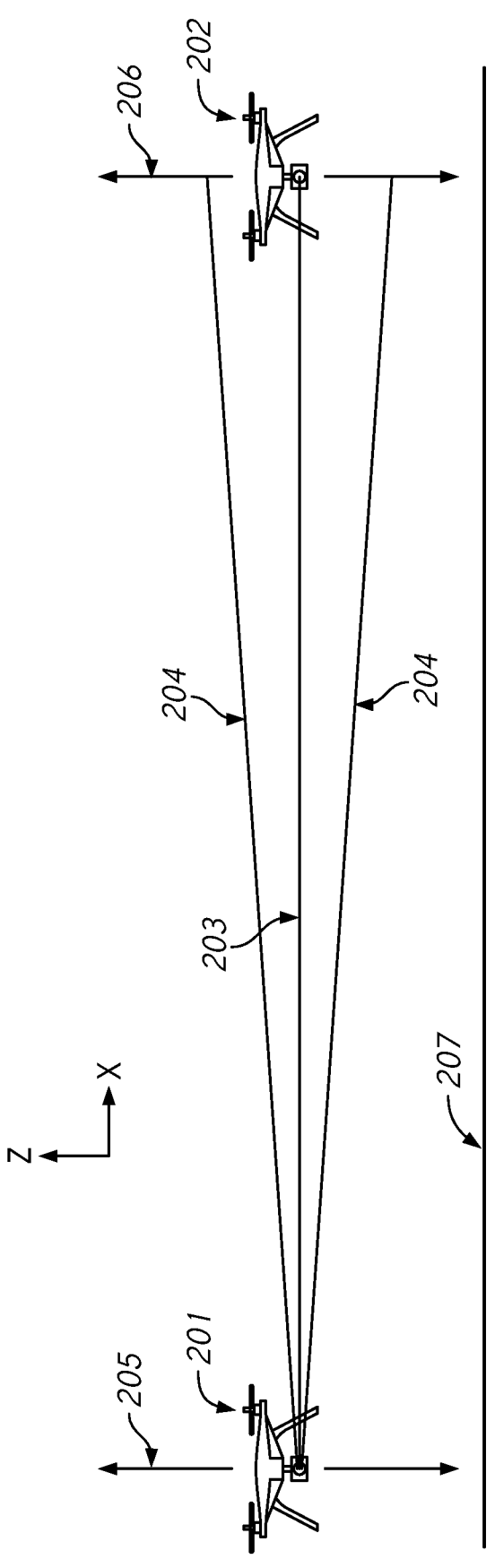
FIG. 2 is a schematic diagram of a measurement system according to some embodiments of the present disclosure.

FIG. 2 is a schematic diagram of a measurement system according to some embodiments of the present disclosure. The measurement system may, in some embodiments, be included in the measurement system 1000 of FIG. 10. The measurement system of FIG. 2 may use a first drone 201 and a second drone 202, each of which may include payloads, which may be similar to the payloads 110/120 of FIG. 1. Drone 201 provides a diverging laser beam 203 towards the second drone 202. The laser beam 203 may have beam divergence angles defined by beam divergence lines 204. The second drone 202 may be equipped with a receiver or a retro-reflector to either receive the laser light or reflect the laser light back to a receiver located on the first drone 201. Drones 201 and 202 fly in coordinated motion along flight paths 205 and 206, respectively. In some embodiments, the coordinated flight paths 205 and 206 may have a vertical component. The vertical component of the flight paths 205 and 206 may provide path-integrated gas concentration measurements as a function of vertical position along the line between drone 201 and drone 202 from just above the ground surface 207 to an altitude above the region of elevated gas being emitted from the equipment, facility or emission source under measurement.

A laser source 101 and transmitter (e.g., as part of transceiver 102) are mounted on drone 201. The receiver may be mounted on drone 202, or a retro-reflector may be mounted on drone 202, in which case the receiver may be mounted on drone 201. The transmitted laser beam 203 may be diverging, with a divergence angle illustrated by lines 204, to reduce the difficulty and/or complexity associated with illuminating the receiver or retro-reflector on drone 202 with transmitted beam 203. The coordinated flight paths 205 and 206 for drones 201 and 202 may be configured to measure the path-integrated gas concentration of the target gas species as a function of the vertical position above ground. The path separating drones 201 and 202, together with the coordinated flight paths 205 and 206 define a flux surface across which the gas concentration and gas flux may be measured. Coordinated flight paths and measurements may be repeated to provide signal averaging or to otherwise improve signal fidelity.

The coordinated flight paths 205 and 206 may be selected to measure the path-integrated gas concentration between the drones from an altitude near ground surface 207 to an altitude above the region of elevated gas being emitted from the equipment, facility or emission source that is being measured. The spatial coordinates of the end points of an integrated gas concentration measurement, and therefore the altitude above ground, may be determined using the drone navigation system, or by any other means, which may include position determination sensors such as GPS, inertial navigation, laser altimeter, laser rangefinder, and/or others. The altitude corresponding to the upper extent of the region of elevated gas concentration may be determined using measurements from the drone-mounted open-path laser spectroscopy system (e.g. when such measurements yield ambient levels), or by other methods. An example coordinated flight may entail both drones increasing altitude at similar rate until they reach their maximum altitude.

Figure 3:
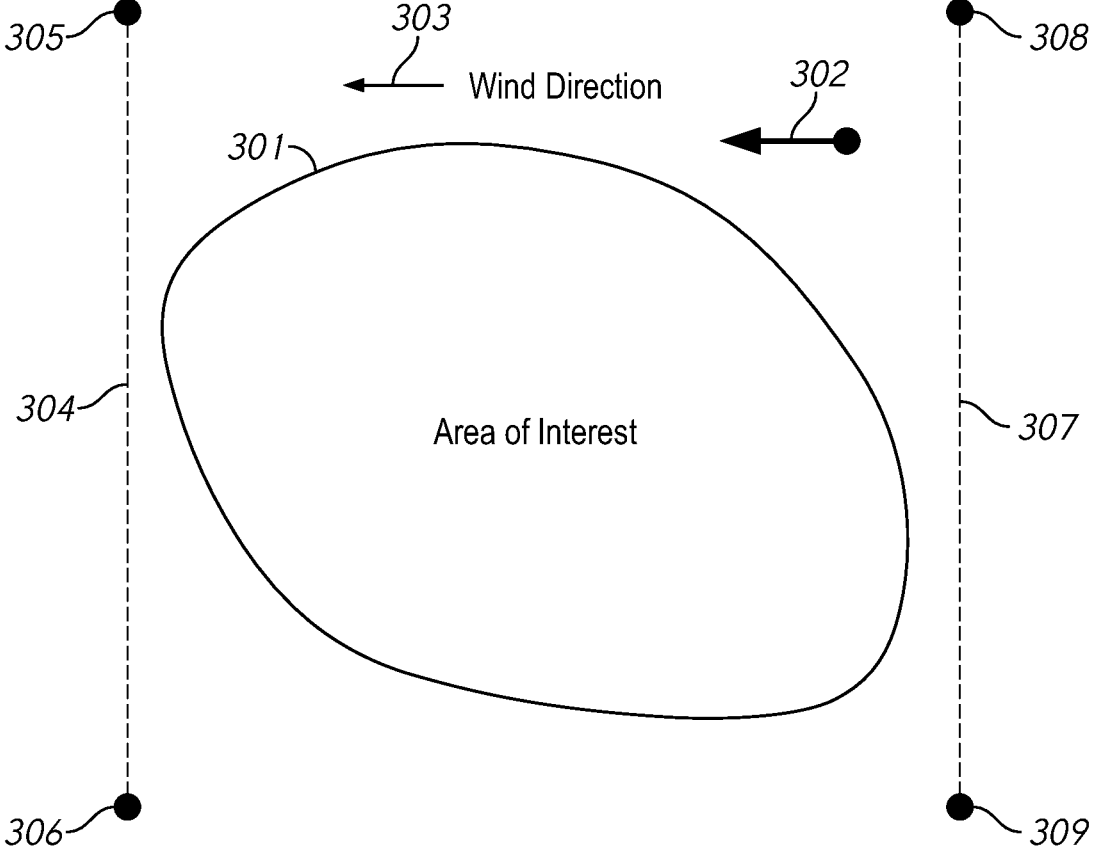
FIG. 3 is a block diagram of a measurement procedure according to some embodiments of the present disclosure.

FIG. 3 is a block diagram of a measurement procedure according to some embodiments of the present disclosure. FIG. 3 represents a particular configuration for measuring gas flux through two flux surfaces 304 and 307 which may be positioned upwind and downwind of an area of interest 301. The measurement procedure of FIG. 3 may be implemented using one or more of the techniques and components described in FIGS. 10, 1, and/or 2. FIG. 3 may represent a 'top down' view of a measurement procedure.

The measurement procedure of FIG. 3 may measure the emission rate of a target gas species from area of interest 301, the area of interest 301 may include one or more emission sources. Wind measurement device 302 is positioned inside or near an emission source (which may be inside area of interest 301) to measure the wind speed and direction 303 while the open-path laser spectroscopy measurements are performed. Alternatively, or in addition, a wind measuring device may be placed on one or more of the drones. Drones 305 and 306 are equipped with an open-path laser spectroscopy device to measure the vertical gas concentration or gas density profiles for the target gas species along flux surface 304, and/or or vertical wind profiles corresponding to the vertical paths (e.g. 305, 306, 308, and/or 309). Drones 308 and 309 are outfitted with an open-path laser spectroscopy device to measure the vertical gas concentration or gas density profiles for the target gas species along flux surface 307.

Gas concentration measurements as a function of vertical position may be performed for flux surfaces upwind and downwind of an emission source for which the gas emission rate is being measured. This type of measurement configuration may be useful for discriminating gas emissions from background or interference emissions and/or isolating the emission source. In the example shown in FIG. 3, a wind speed and direction measuring device 302 is placed within, or near, the area of interest 301 (shown looking downward onto the emission source) to measure the wind speed and direction 303 in the area around the emission source (which may be within or near the area of interest 301). Alternatively, or in addition, a wind measuring device may be placed on one or more of the drones. More than one wind measurement device may be deployed in to improve estimates of the wind speed and direction as a function of horizontal and/or vertical position. The gas concentration measurement surfaces 304 and 307 (the vertical dimension of the surfaces is out of the page in FIG. 3) are positioned downwind and upwind of the area of interest 301. It may be useful to choose locations for the flux surfaces such that the wind field within the flux surface region is relatively unobstructed by objects. If obstructions or other factors cause the wind field to vary appreciably in the horizontal dimension, then the separation between the drones may be reduced to lessen this effect. In some embodiments, the drone separation may be chosen to be the largest separation such that the wind speed and direction do not change appreciably between the drones.

The downwind flux surface 304 is formed by drones 305 and 306 at respective locations along their coordinated flight paths and carrying an open-path laser spectroscopy system. The upwind measurement surface 307 is formed by drones 308 and 309 at respective locations along their coordinated flight and carrying an open-path laser spectroscopy system. Gas concentration measurements across flux surfaces 304 and 307 may be performed simultaneously with two coordinated flight gas concentration measurement systems. To enable arbitrarily large number of simultaneous drone measurements, each drone may be equipped with a transmitter and a receiver (e.g. directed forward) for a first measurement set, and a retro-reflector (e.g. directing the retro-reflected beam backwards) to enable a second measurement set. Flux surfaces 304 and 307 are shown vertical, planar and parallel to one another. However, flux surfaces may include any surface whatsoever, including any shape, size, or orientation. While it may be advantageous to perform measurements corresponding to different flux surfaces simultaneously, measurements corresponding to different flux surfaces may be performed at any times. In some embodiments, improved accuracy gas flux estimates may be achieved by delaying the downwind flux surface measurement relative to the upwind gas flux surface measurement by the gas transit time between the two flux surfaces. The transit time may be estimated by dividing the average distance between the measurement surfaces by the average wind speed at the altitude corresponding to the center-of-mass altitude of the elevated gas concentration distribution.

The positioning and extent of the upwind and downwind surfaces for gas concentration measurements may be designed to capture substantially all gas entering or exiting the area of interest based on the local wind direction, including fluctuations of the wind directions. Wind speed and direction data may be used to design the drone deployment locations and open-path laser spectroscopy equipment, and to define the coordinated flight paths for the drones to capture substantially all gas emitted by the emission source. In some cases, accounting for fluctuations in the wind direction may require deployment of more than one flux surface downwind and/or upwind of the emission source.

Figure 4:
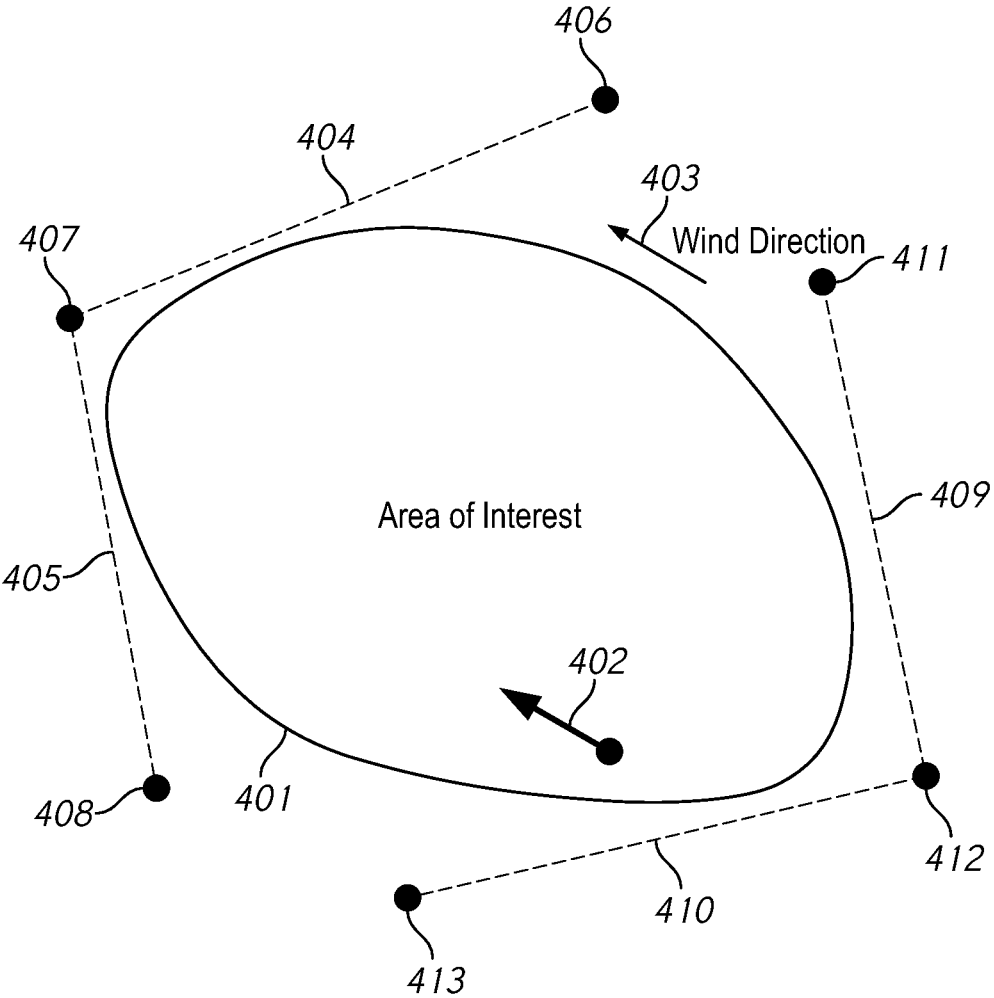
FIG. 4 is a block diagram of a measurement procedure according to some embodiments of the present disclosure.

FIG. 4 is a block diagram of a measurement procedure according to some embodiments of the present disclosure. The measurement procedure of FIG. 4 may generally be similar to the measurement procedure of FIG. 3, except that in the measurement procedure of FIG. 4, multiple upwind flux surfaces 409 and 410 and multiple downwind flux surfaces 404 and 405 are used. For the sake of brevity, features and operations previously described with respect to FIG. 3 will not be repeated again. The measurement procedure of FIG. 4 may include operations or components similar to those discussed in FIGS. 10, 1 and/or 2.

FIG. 4 shows a measurement configuration with two flux surfaces downwind of the emission source and two flux surfaces upwind of the emission source. This configuration may be implemented, for example, using two groups of three drones each undergoing coordinated flight to perform the open-path laser spectroscopy measurements used to determine the gas concentration as a function of vertical position for two flux surfaces upwind and two flux surfaces downwind of the emission source, which may be located within area of interest 401. For the downwind measurement, the flux surfaces 404 and 405 are defined by the positions of drones 406, 407 and 408 throughout the duration of their coordinated flight. Similarly, for the upwind measurement, the flux surfaces 409 and 410 are defined by the positions of drones 411, 412 and 413 throughout the duration of their coordinated flight. For this embodiment, a wind measurement device 402 is positioned inside or near area of interest 401 to measure the vertical wind profiles 403 while the open-path laser spectroscopy measurements are performed. Alternatively, or in addition, a wind measuring device may be placed on one or more of the drones.

Two flux surfaces 404 and 405 are positioned downwind of the area of interest 401, and two flux surfaces 409 and 410 are positioned upwind of the emission source. This configuration may be implemented using groups of multiple drones undergoing coordinated flight to perform the open-path laser spectroscopy measurements, as described in more detail in FIG. 5.

Figure 5:
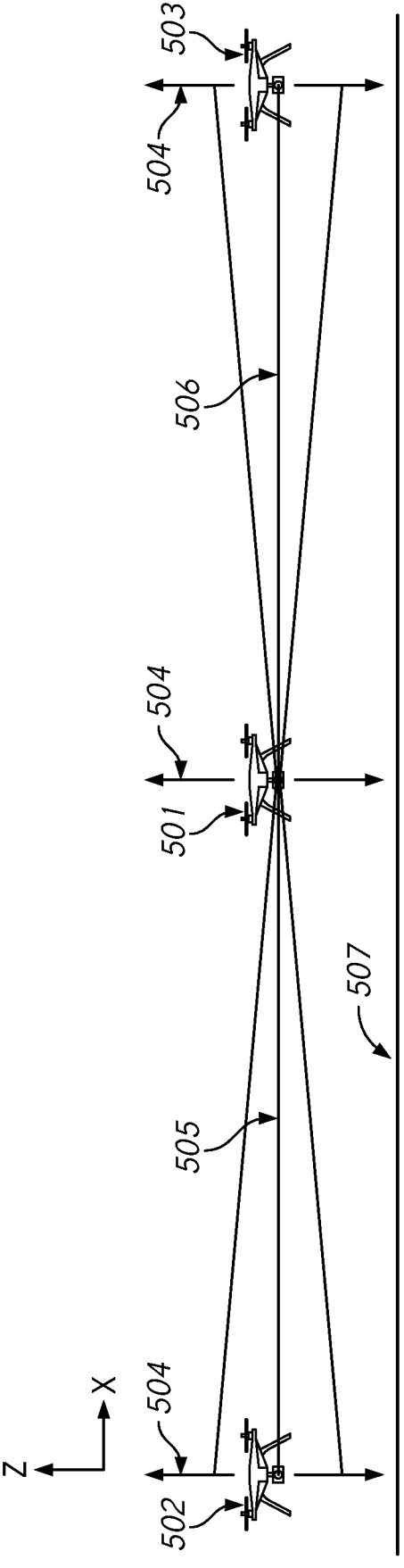
FIG. 5 is a schematic diagram of a measurement system using more than two mobile platforms according to some embodiments of the present disclosure.

FIG. 5 is a schematic diagram of a measurement system using more than two mobile platforms according to some embodiments of the present disclosure. The measurement system of FIG. 5 may generally be similar to the measurement system of FIG. 2, except that the measurement system of FIG. 5 includes three mobile platforms 501, 502 and 503 instead of two mobile platforms. For the sake of brevity, features and components previously described with respect to FIG. 2 will not be described again with respect to FIG. 5. The measurement system may include mobile platforms 501-503, any of which may use one (or both) of the payloads 110 and 120 of FIG. 1.

FIG. 5 shows a measurement system using three drones to measure path-integrated gas concentration along the line between drone 501 and 502 and the line between drone 501 and 503. The drones fly in coordinated motion along trajectories 504 to measure path-integrated gas concentration as a function of vertical position along the lines between the drones from just above the ground surface 507 to an altitude above the region of elevated gas being emitted from the emission source.

In this example, three drones undergo coordinated flight while measuring the path-integrated gas concentration along the line 505 between drones 501 and 502 and the line 506 between drones 501 and 503. The drones may fly in coordinated motion along trajectories 504 to measure path-integrated gas concentration as a function of vertical position along the lines between the drones from an altitude just above the ground surface 507 to an altitude above the region of elevated gas being emitted from the equipment, facility or emission source under measurement. In some embodiments, the trajectories may be more or less vertical.

Wind measuring devices may be placed on one or more of the drones to measure vertical wind profiles. A wind profile corresponding to a first flux surface may differ from a wind profile corresponding to a second flux surface. Any wind data (e.g. fixed measured, mobile measured, or inferred) may be used and combined in any way (e.g. weighting) to determine a spatial wind profile.

Figure 6:
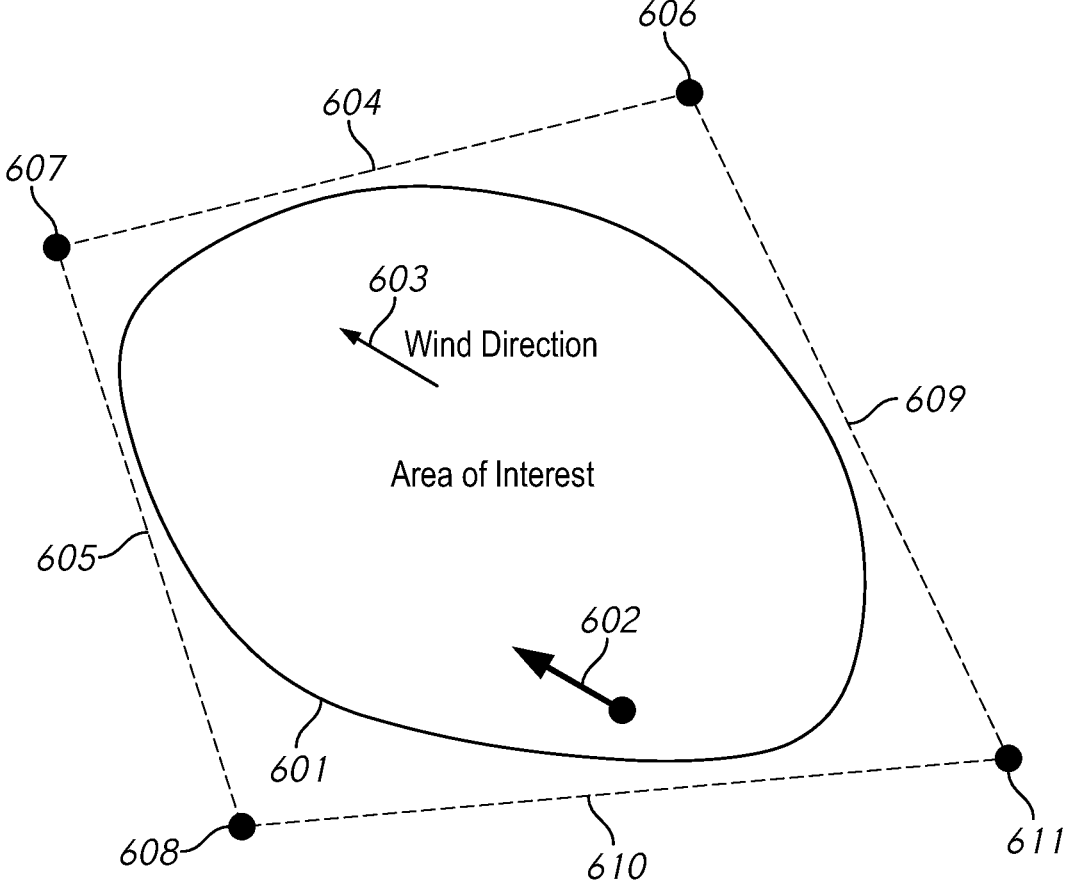
FIG. 6 is a block diagram of a measurement procedure according to some embodiments of the present disclosure.

FIG. 6 is a block diagram of a measurement procedure according to some embodiments of the present disclosure. The measurement procedure of FIG. 6 may generally be similar to the measurement procedures of FIGS. 3-4. For the sake of brevity, features and components previously described with respect to FIGS. 3-4 will not be repeated again with respect to FIG. 6. FIG. 6 shows a measurement procedure where flux is measured through measurement surfaces which surround (or substantially surround) an area of interest 601, which may contain an emission source.

The measurement procedure may be carried out by one or more of the mobile platforms and payloads described herein. The example of FIG. 6 shows four drones are used to perform the open-path laser spectroscopy measurements that are used to determine the gas flux through a surface that encloses the entire perimeter of the area of interest 601, or at least the gas emissions source. The downwind portions of the surface 604 and 605 are defined by the positions of drones 606, 607 and 608 throughout the duration of their coordinated flight trajectories. Similarly, the upwind portions of the measurement surface 609 and 610 are defined by the positions of drones 611, 606 and 608 throughout the duration of their coordinated flight. For this embodiment, wind measurement device 602 is positioned inside or near area of interest 601 to measure the wind speed and direction 603 while the open-path laser spectroscopy measurements are performed. Alternatively, or in addition, a wind measuring device may be placed on one or more of the drones.

In some cases, using flux surfaces which enclose (or substantially enclose) the area of interest 601 may help to measure most or all of the gas emitted from the area of interest 601 and/or the emissions source. In the example of FIG. 6, four drones are used to perform the open-path laser spectroscopy measurements to determine the gas flux through a surface that encloses the entire perimeter of the area of interest 601, although more or fewer drones may be used in other embodiments. The downwind portions of the flux surfaces 604 and 605 are defined by the positions of drones 606, 607 and 608 throughout the duration of their coordinated flight trajectories. Similarly, the upwind portions of the flux surfaces 609 and 610 are defined by the positions of drones 611, 606 and 608 throughout the duration of their coordinated flight. A wind measurement device 602 may be positioned near an area of interest 601 to measure the wind speed and direction 603 while the open-path laser spectroscopy measurements are performed. Alternatively, or in addition, a wind measuring device may be placed on one or more of the drones to directly determine a vertical wind profile.

The wind speed and direction data may be used determine spatial (e.g. vertical) wind profiles (e.g. wind speed and/or direction) for use in computing gas fluxes through flux surfaces. The wind speed and direction at the location of the gas concentration measurements may be estimated from several sources including but not limited to in-situ sensor(s), local weather stations, and weather models. The wind speed may vary significantly as a function of vertical height above ground. To account for this phenomenon, it may be advantageous for wind speed information to be specified for a specific height above ground. However, the gas plume may be located at a different height, or may be distributed over a range of heights, above ground. Because wind speed may be critical for accurately determining gas flux, a method for reliably relating the wind speed at one height to another may be required to produce an accurate gas flux estimate.

Figure 7:
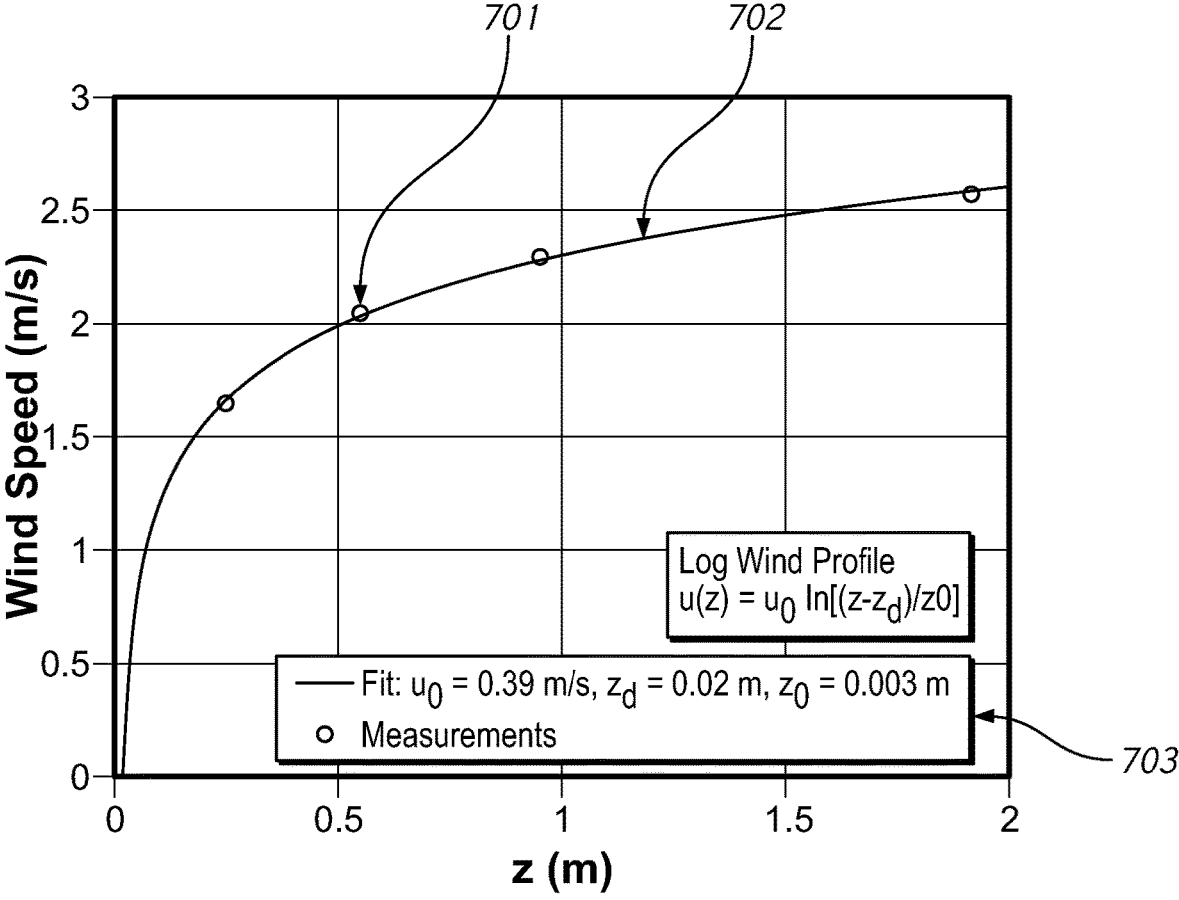
FIG. 7 is a graph of wind speed with respect to height above ground according to some embodiments of the present disclosure.

FIG. 7 is a graph of wind speed with respect to height above ground according to some embodiments of the present disclosure. The graph includes measurements 701 of wind speed a different heights above ground fitted with a logarithmic wind profile 702. The logarithmic wind profile equation and parameters 703 can be used to relate wind speed information at one height above the ground surface to a different height above the ground surface.

FIG. 7 shows a vertical wind speed profile from anemometer measurements 701 at four heights above ground fitted with a logarithmic profile 702. More or fewer measurement heights, or a different fitting profile may be used in other example embodiments. The functional form of the logarithmic wind speed profile may be represented by:

$$\vec{u}(z) = u_0 \ln\left(\frac{z - z_d}{z_0} + \psi(z, z_0, L)\right)\hat{u}, \qquad \text{Eqn. 1}$$

where u0 is the velocity coefficient, z is the height above ground, zd is the zero-plane displacement, z0 is the surface roughness parameter, v is the atmospheric stability parameter and L is the Obukhov length. The measurements 701 are taken at four different heights above ground, and the logarithmic wind speed profile shown in equation 1 is used to determine the coefficient values. Neutral stability conditions are assumed for fitting the data, such that $\psi=0$, and the resulting fit parameters 703 are shown in the inset of graph. The inset also shows example parameters which were fitted using the wind model. Other values of the fitting parameters may be used in other example parameters. Acquiring measurements of the wind speed and direction at different heights above ground may be a reliable method for determining the wind speed and direction as a function of height, in cases where it is practical to do so.

In some embodiments, a wind measuring device is attached to a mobile platform, such as a drone, may be useful to perform direct measurements of spatial (e.g. vertical) wind profiles. Also, the attitude (e.g. pitch, roll, and/or yaw) of a drone in the presence of a wind field may be used to determine wind data. A drone used for measuring wind data may be the same or different from a drone used for measuring a vertical gas concentration dependence. Measurement or determination of wind data using drones in any way may replace or be combined with any other measurement or determination of wind data in any way.

For some gas leak quantification measurement scenarios wind speed versus height data may not be available, and estimates for the values of zd and z0 may be required to formulate a logarithmic wind profile. In this case values for zd and z0 may be estimated using basic rules and/or tables that specify the surface roughness for various terrain types and observations of measurement scene terrain type. In general, zd may be approximated as $\frac{2}{3}$ of the average height of obstacles in the measurement scene. A rough approximation for z0 may be computed as $\frac{1}{20}$ the average height of obstacles in the measurement scene. A more refined value for z0 may be derived using tables that list the accepted value of z0 for a wide variety of terrain types. Furthermore, 3D lidar, photogrammetry, or other methods, may be used to create a digital elevation model (which is a 3D computer graphics representation of a terrain's surface that may be created from a terrain's elevation data) of the ground surface in the region where the flux estimate is performed. Direct measurements of the variations in ground surface height, vegetation height and the height of structures in the measurement scene may result in further improvements to estimates of the z0 parameter. An example procedure for relating wind speed (u(z1)) available at height (z1) above ground to another height above ground (z2) may include estimating values of $z_d$, $z_o$ and $\psi$ based on terrain observations and/or 3D topography information such as a digital elevation model and using equation (1) to compute u($z_2$).

In cases where the flux surface comprises, or is near, complex topography, improved wind speed and direction information as a function of space and/or time may be desired. It may be possible to determine improved wind speed and data estimates for locations corresponding to the flux surface by performing computational fluid dynamics simulations based on measured input data including, but not limited to, wind speed and direction data, ground topography data, surface roughness data and others.

Once the gas concentration as a function of vertical position and the wind speed and direction as a function of vertical position have been determined for a measurement surface, the gas flux ($\Phi_s$) through a measurement surface may be determined using Equation 2, below:

$$\Phi_s = \sum_z^{N_z} \rho_z \hat{n} \cdot \vec{u}_z \Delta z \qquad \text{Eqn. 2}$$

Here, $\rho_z$ is the path-integrated gas density along the flux surface at a height z above the ground surface, $\vec{u}_z$ is the wind velocity at a height z above the ground surface passing through the flux surface, $\hat{n}$ is a unit vector in the direction normal to the flux surface pointing away from the emission source and $\Delta z$ is the spacing between adjacent path-integrated gas density measurements in the vertical dimension. The total gas flux (e.g., the gas emission rate) for the emission source ($\Phi_{aoi}$) may then be determined using Equation 3, below:

$$\Phi_{aoi} = \Phi_{s_{downwind}} + \Phi_{s_{upwind}} \qquad \text{Eqn. 3}$$

where $\Phi\_(s\_downwind)$ is the gas flux through the downwind measurement surface(s) and $\Phi\_(s\_upwind)$ is the gas flux through the upwind flux surface(s). Example profiles for vertical wind speed and gas density profiles for upwind and downwind flux surfaces are shown in FIG. 8. Profiles like these may be used as inputs to equation 2 to determine the flux through a flux surface. Subsequently, the upwind and downwind gas flux results may be combined using equation 3 to determine the emission rate or sequestration rate for the emission source.

Figures 8C, 8D:
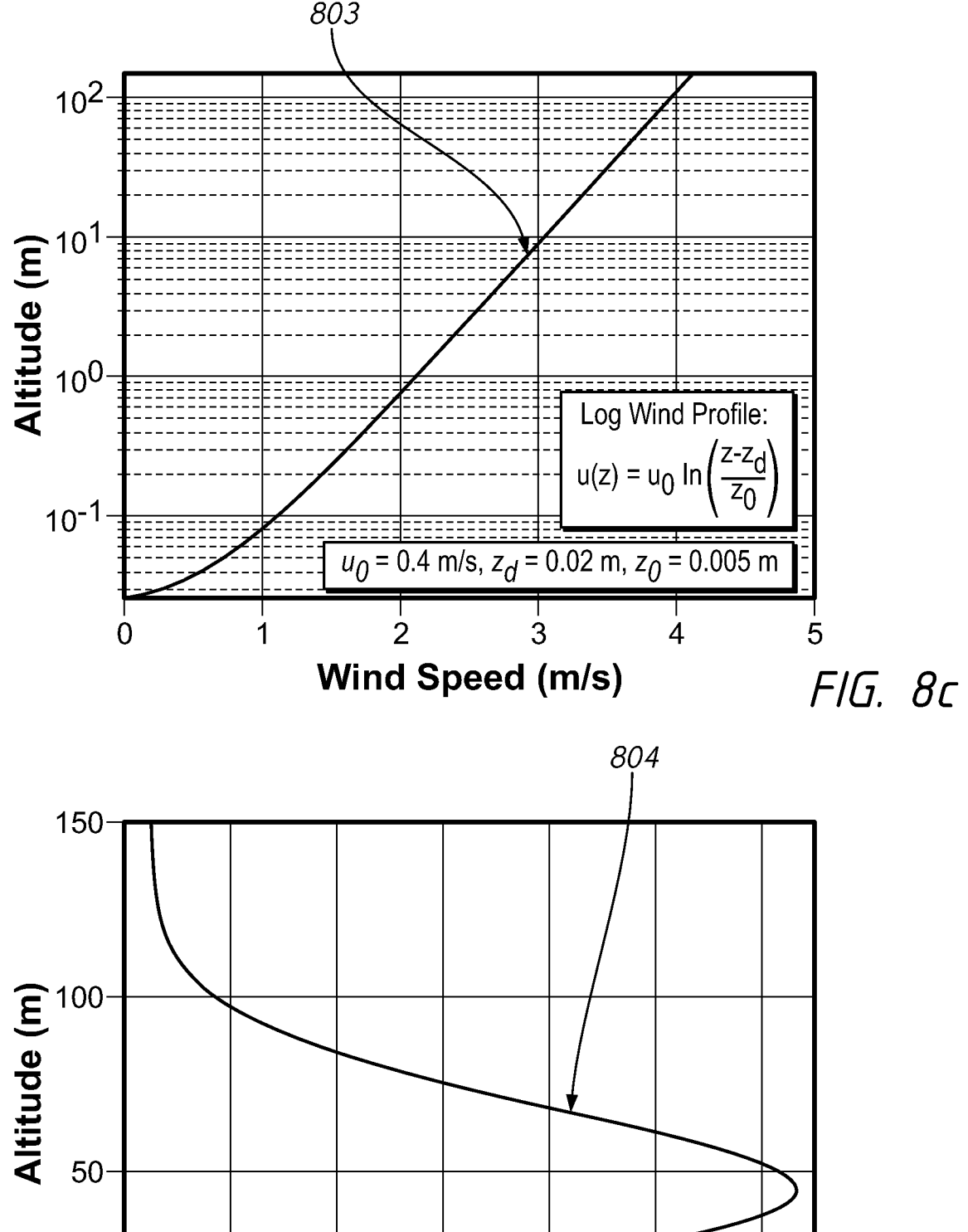

FIGS. 8A-8D are a set of graphs showing wind speed and gas density profiles for flux surfaces upwind and downwind of an area of interest according to some embodiments of the present disclosure. Graphs 801 and 803 show example wind speed profiles versus altitude upwind and downwind of an area of interest, respectively, and graphs 802 and 804 show path-integrated gas density profiles versus altitude for a gas flux measurement surfaces located upwind and downwind of an emission source. The graphs of FIG. 8 may, in some embodiments, be collected by one or more of the measurement systems and procedures described herein. FIG. 8C shows an inset with a wind model and fit parameters for that model. Other fit parameter values may be used in other embodiments.

The example vertical gas density profiles in FIG. 8 show a scenario where the gas species being measured has a non-negligible nominal (e.g. background or ambient) atmospheric concentration. Here, it may be advantageous to ensure the upwind flux surface projects, along the wind direction, to a similar same area as the downwind flux surface such that the flux determined for the emission source is not biased by the nominal atmospheric concentration of the target gas species. It may also be possible to account for differences in area of the upwind and downwind measurement surfaces by measuring the areas (or vector components of the area vectors in the directions of the wind vector) of the upwind and downwind flux surfaces as well as the nominal atmospheric concentration of the target gas species near the emission source. The gas flux contribution from the nominal atmospheric concentration of the target gas species may then be subtracted from a gas flux measurement containing gas flux from the emission source. The flux estimates for the upwind and downwind measurement surfaces may be scaled according to their projected area along the wind direction to reduce bias in the flux estimate for the emission source. The areas of the measurement surfaces may be determined by 1) measuring the locations of the drones during flight using their navigation systems, 2) laser radar measurements between the drones during flight, or 3) by any other methods.

Figure 9:
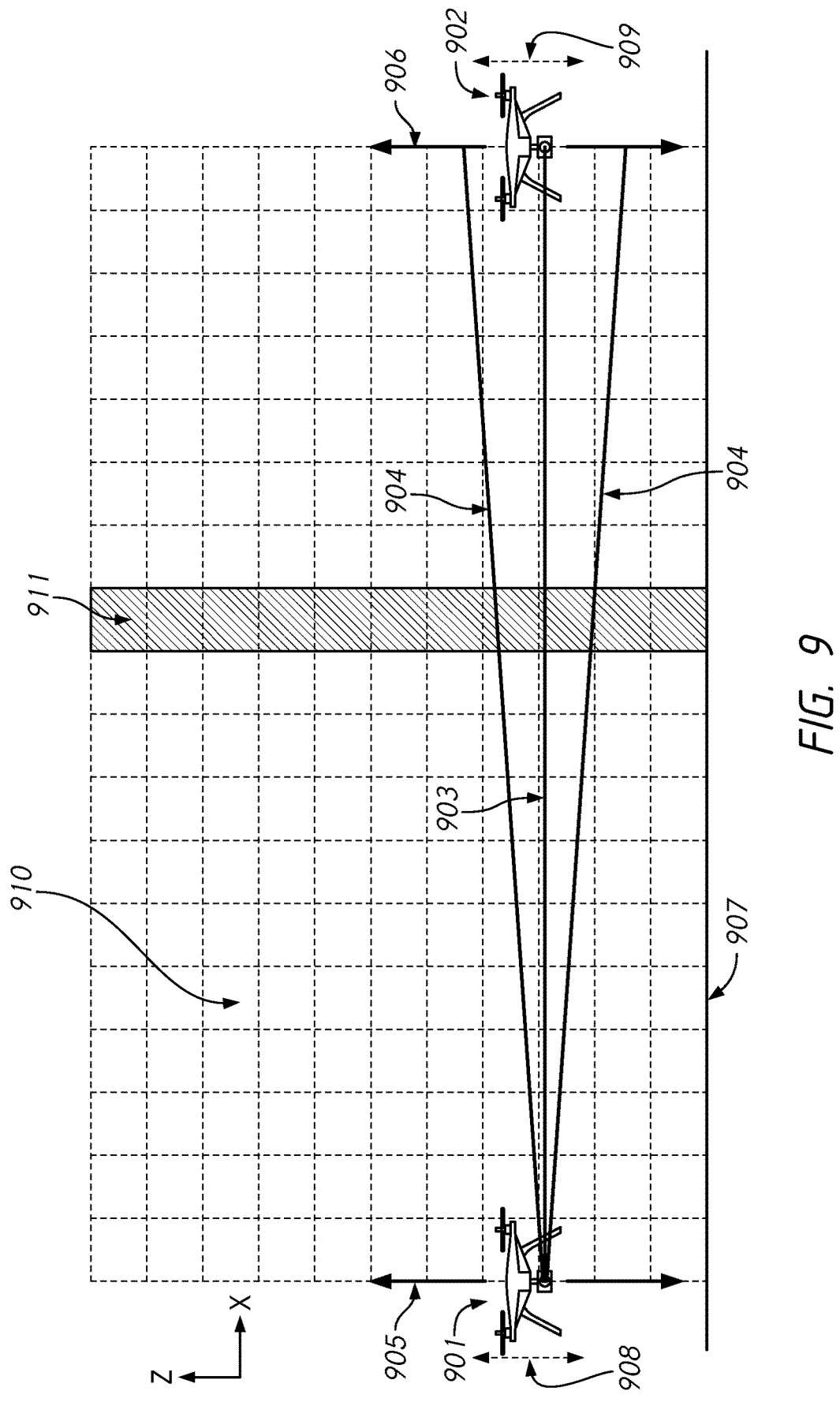
FIG. 9 is a schematic diagram of tomographic measurements based on mobile platforms according to some embodiments of the present disclosure.

FIG. 9 is a schematic diagram of tomographic measurements based on mobile platforms according to some embodiments of the present disclosure. FIG. 9 shows a measurement system which may be generally similar to the measurement systems of FIGS. 10, 2, and/or 5, except that the measurement system of FIG. 9 may collect tomographic information. In some embodiments, the measurement system of FIG. 9 may include similar hardware as other measurement systems described herein, but may differ in its measurement procedure and/or software instructions. For the sake of brevity, features and components of the measurement system similar to those previously described will not be described again.

Drone 901 transmits a diverging laser beam 903 with beam divergence angles defined by beam divergence lines 904 is transmitted to drone 902, which is equipped with a receiver or a retro-reflector to either receive the laser light or reflect the laser light back to a receiver located on drone 901. Drones 901 and 902 fly in coordinated motion along vertical trajectories 905 and 906, respectively. During flight, drones 901 and 902 undergo additional vertical motions 908 and 909 to allow acquisition of path-integrated gas concentration measurements between drones 901 and 902 at various angles with respect to the horizontal direction (x-direction). The common portion of the vertical flight trajectories 905 and 906 are designed to provide path-integrated gas concentration measurements as a function of vertical position along the line between drone 901 and drone 902 from just above the ground surface 907 to an altitude above the region of elevated gas being emitted from the emission source. The path-integrated gas concentration measurements acquired in this way may be used to tomographically reconstruct the gas concentration as a function of horizontal (x) and vertical (z) position.

Tomographic reconstruction of path-integrated gas concentration measurements may enable improved localization of the gas concentrations within a flux surface and may lead to more accurate flux determinations by enabling more accurate application of the wind speed and direction data for computing Ps. An example embodiment of a method for acquiring path-integrated gas concentration measurements that may be suitable for tomographic reconstruction to determine gas concentration distributions as a function of vertical position (z) and horizontal position (x) within the flux surface is described herein. In this example, an open-path laser spectroscopy measurement system is deployed using two drones undergoing coordinated flight. Drone 901 transmits a diverging laser beam 903 with beam divergence angles defined by lines 904 is transmitted to drone 902. Drone 902 may be equipped with a receiver or a retro-reflector to either receive the laser light or reflect the laser light back to a receiver located on drone 901. Drones 901 and 902 fly in coordinated motion along vertical trajectories 905 and 906, respectively. During flight, drones 901 and 902 undergo additional vertical motions 908 and 909 to allow acquisition of path-integrated gas concentration measurements between drone 901 and 902 at various angles with respect to the horizontal direction (x-direction). To obtain various angles, which may be necessary for tomographic reconstruction, trajectories 905 and 906 may be such that drones 901 and 902 are not always at the same vertical height. The drone motion may be staggered such that one drone moves vertically upward (or downward) a certain distance and pauses, then the other drone moves vertically upward (or downward), then pauses. Other flight paths are also possible.

Additional vertical motions 908 and 909 may be anti-correlated for efficient acquisition of path-integrated gas concentration as a function of angle with respect to the horizontal direction. In general, any drone motion may be used that produces variation in measurement angle. The common portion of the vertical flight trajectories 905 and 906 (e.g. the points where the drone heights are the same) may be designed to provide path-integrated gas concentration measurements as a function of vertical position along the line between drone 901 and drone 902 from just above the ground surface 907 to an altitude above the region of elevated gas being emitted from the equipment, facility or emission source under measurement, as previously described. The path-integrated gas concentration measurements acquired in this way may be used for tomographic inversion of the path-integrated gas concentration measurements such that a gas concentration is determined for each grid cell 910 using the equation, $$b_i = \sum_j^N A_{ij} c_j \qquad \text{Eqn. 4}$$

Here, $b_i$ is the path-integrated gas concentration measurement along the $i^{th}$ measurement direction, $A_{ij}$ is the chord length along the $i^{th}$ direction inside the $j^{th}$ grid cell and $c_j$ is the gas concentration in the $j^{th}$ grid cell. In some cases, it may be difficult to acquire enough concentration measurements ($b_i$) to invert equation 4 directly. Based on the drone flight parameters and/or transmitted beam parameters (divergence parameters and possibly beam scanning parameters), it may be impractical to acquire sufficient spatial resolution for direct inversion of equation 4. It may also be the case that measurement acquisition duration is sufficiently long that the gas distribution evolves during the measurement duration, and as a results direct inversion of equation 4 is not possible. This problem may be overcome by rapidly acquiring coarse spatial resolution measurements and applying one of a number of techniques for spanning the null space of an under-sampled reconstruction grid.

Once the flux for individual columns ($\Phi_x$) 911 have been estimated, the total gas flux corresponding to a flux surface may be determined. Gas flux ($\Phi_x$) for each column may then be integrated to determine the total gas flux for the measurement surface ($\Phi_s$) using equation 5, below:

$$\Phi_s = \sum_x^{N_x} \Phi_x \Delta x \qquad \text{Eqn. 5}$$

Here, $\Delta x$ is the grid cell size in the horizontal direction and $N_x$ is the number of vertical columns being integrated. The vertical column flux measurements integrated to determine the total flux from an emission source may comprise one or many flux surfaces, and may or may not enclose the gas emission source.

FIG. 11 is a flow chart depicting a method according to some embodiments of the present disclosure. The method 1100 may represent a method of determining a total gas flux through a flux surface. In some embodiments, the method 1100 may be repeated for one or more flux surfaces about an emission source (or suspected emission source). The method 1100 may be performed using one or more of the procedures or measurement systems described herein.

The method 1100 may generally begin with box 1110 which describes translating a first drone along a first motion path and a second drone along a second motion path. The first drone and the second drone may be mobile platforms (e.g., 1001/1002 of FIG. 1). The mobile platforms may receive instructions for the first and second motion paths from an external controller (e.g., a base station) and/or may store instructions for the first and the second motion paths in an internal memory. In some embodiments, the first and the second drones may communicate with each other (e.g., directly and/or through a base station) to coordinate the motion of the first motion path and the second motion path.

In some embodiments, the first motion path and the second motion path may be generally vertical. In some embodiments, the first motion path and the second motion path may involve the first and the second drones rising at similar rate, such that a measurement path between the drones remains generally parallel to the surface of the ground between the drones.

Box 1110 may generally be followed by box 1120, which describes performing a gas measurement along a measurement path between the first drone and the second drone at respective first positions along the first and the second motion paths. In some embodiments, as the first drone and the second drone travel along the first and second motion paths, respectively, they may stop (or slow down) at their respective first positions in order to perform the measurement. In some embodiments, the first position may represent a moment in time when a measurement is taken, and the movement of the drones may be generally continuous.

The gas measurement may be performed based on a laser beam (or other light source) which travels between the two drones. In some embodiments, a transmitter on the first drone may direct the laser beam to a receiver on the second drone. In some embodiments, the transmitter and receiver may both be located on the first drone, and the second drone may include a reflector, such as a retroreflector, which returns all or a portion of the laser beam back to the first drone. The transmitted and received light may be compared to determine a concentration of the gas along the measurement path. In some embodiments, the length of the measurement path (e.g., a distance between the transmitter and receiver) may be determined. For example, a distance between the drones may be measured using a range finder and/or positioning data (e.g., from GPS) of the drones. In some embodiments, a wavelength of the laser beam may be chosen based on a particular target gas. Accordingly, box 1120 may include determining the gas concentration of the target gas along the measurement path. The gas measurement may be an integrated-path gas concentration measurement. The gas measurement may be made using one or more computing devices (e.g., circuitry and/or one or more processors that execute instructions for performing a gas measurement in accordance with techniques described herein).

The method 1100 may also include box 1130, which describes measuring or inferring wind data corresponding to a vertical height above ground of the measurement path. Box 1130 may be performed before, during, after, or combinations thereof, boxes 1110 and 1120. For example, in some embodiments, the wind data may be determined simultaneously to the gas measurement being performed, while in some embodiments the wind data may be determined prior to the first and second drones moving to the first position.

The wind data may include information such as wind direction and wind speed at the height of the measurement path. In some embodiments, the wind data may be determined, at least in part, by one or both of the first drone and second drone. For example, a sensor, such as an anemometer, may be mounted on one or both of the drones and may record the wind data at the first position. In some embodiments, the wind data may be based on attitude information of the first drone or the second drone. In some embodiments the wind data may be determined, at least in part, by information obtained from outside the drones. For example, the wind data may be determined from a sensor located at location off the drones (e.g., located on the emission source). In some embodiments, wind data may not be directly measured for the height of the measurement path, but the wind data may be inferred based on one or more measured wind data at other heights. For example, a wind model may be fitted to one or more measured data points, and the wind model may be used to calculate the wind data at the height of the measurement path. In some embodiments, multiple wind measurement methods may be combined.

Boxes 1120 and 1130 may generally be followed by box 1140, which describes calculating a gas flux based on the wind data and the gas measurement. The calculating may include combining a wind speed from the wind data and a gas concentration from the gas measurement to find a gas flux density, and then multiplying the gas flux density by an incremental height to find the gas flux. The incremental height may represent a vertical spacing between a first and second measurement path, may represent a height of a flux surface, or any other distance to represent a vertical width associated with a measurement path. The gas flux may be calculated using processing circuitry and/or one or more processors able to execute instructions for calculating a gas flux in accordance with techniques described herein.

In some embodiments, the method 1100 may be repeated at several different positions. For example, the method 1100 may involve repeating the boxes 1120-1140 at a plurality of positions of the two drones, which may provide a plurality of measurement paths. For example, this may include performing a gas measurement at a second measurement path which corresponds to a second position of the first and second drone along the first and second motion paths, and measuring or inferring wind data corresponding to the vertical height of the second measurement path. A second gas flux may then be calculated for the second measurement path.

In some embodiments, the method 1100 may include calculating a total gas flux through a flux surface based on the gas fluxes along one or more measurement paths. For example, the flux surface may be defined by first and the second motion paths. The total gas flux may be found by summing the gas flux measurements for each of the one or more measurement paths. For example, the gas concentrations may represent a vertical gas concentration distribution, which may be associated with a height of a vertical wind profile. The total gas flux may be calculated by processing circuitry and/or one or more processors able to execute instructions for calculating the total gas flux in accordance with techniques described herein. In some embodiments, the total gas flux may be found by finding the gas flux density for one or more measurement paths and integrating along the vertical dimension. For example, the vertical gas concentration profile and vertical wind profile may be combined and integrated along a height axis (e.g., similar to Equation 2, but as an integral rather than as a sum).

In some embodiments the method 1100 may include measuring the total gas flux through more than one flux surface. In some embodiments, additional drones may be used to collect measurements along additional measurement paths. In some embodiments, the first drone and the second drone may reposition to take measurements which are part of a different flux surface. For example, a first total gas flux may be determined for a first flux surface which is upwind of the emission source and a second total gas flux may be determined for a second flux surface which is downwind of the emission source. The method 1100 may include determining a rate at which a target gas is emitted from the emission source based on the first total gas flux and the second total gas flux. For example, the emission rate may be based on a difference between the second total gas flux and the first total gas flux. In some embodiments, the method 1100 may be repeated for a plurality of gas flux surfaces which surround or substantially surround the emission source.

In some embodiments, the method 1100 may involve tomographically reconstructing gas flux information. The tomographic reconstruction may include gas flux information along a vertical and horizontal axis of the flux surface. The drones may collect gas measurements at a variety of angles with respect to the flux surface. For example one or both of the drones may vary their height relative to the other drone in order to change the angle of the measurement path between the drones. The tomographic reconstruction may be based, at least in part, on the measurements at the variety of angles.

Accordingly, examples of systems and methods may calculate gas flux information through a flux surface. In some examples, multiple measurements may be taken of gas flux through multiple surfaces. In this manner, a total measurement of gas emissions from a source (e.g., a pipeline leak, a landfill, a city, a processing facility, a seepage region, storage facility, a geological formation, a location, etc.) may be made. The measurements may be displayed (e.g., visualized) using one or more display devices. One or more actions may be taken based on the measurements. For example, fines may be levied or removed, an operation of the emission source may be changed, environmental impacts may be monitored, a leak or other damage may be remediated, or combinations thereof.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An apparatus comprising:
a first drone configured to follow a first motion path;
a second drone configured to follow a second motion path;
an optical system including a source and receiver configured to measure a gas concentration measurement along a measurement path between the first drone and the second drone; and
a processor configured to collect a plurality of the gas concentration measurements along a plurality of measurement paths, wherein at least two of the plurality of measurement paths are not parallel to each other, and wherein the processor is configured to reconstruct a gas concentration as a function of horizontal and vertical positions across a surface based, at least in part, on the at least two of the plurality of measurement paths that are not parallel to each other and their associated gas concentration measurements,
wherein the processor is further configured to determine the angles of the plurality of measurement paths between the drones, and wherein the reconstruction of the gas concentration as a function of horizontal and vertical positions across a surface is based, at least in part, on the angles of the plurality of measurement paths between the drones and their associated gas concentration measurements.

2. The apparatus of claim 1, wherein the processor is further configured to:
determine wind data corresponding to at least one of the plurality of the gas concentration measurements;
determine a gas flux through the surface based on the plurality of gas concentration measurements and the wind data.

3. The apparatus of claim 2, further comprising at least one wind measurement device positioned on at least one of the first drone or the second drone,
wherein the wind measurement device is configured to collect at least one wind measurement, and
wherein the processor is configured to determine the wind data based, in part, on the at least one wind measurement.

4. The apparatus of claim 3, wherein the wind measurement device is configured to collect a first wind measurement at a first height and a second wind measurement at a second height.

5. The apparatus of claim 1, wherein the source and receiver are positioned on the first drone, and wherein a reflector is positioned on the second drone.

6. The apparatus of claim 1, further comprising:
a first sensor configured to determine a position of the first drone; and
a second sensor configured to determine a position of the second,
wherein the processor is further configured to reconstruct the gas concentration as a function of horizontal and vertical positions across a surface based, at least in part, on the positions of the first drone and the second drone.

7. The apparatus of claim 1, wherein the surface is a substantially vertical surface.

8. The apparatus of claim 1, wherein the source is positioned on the first drone and wherein the receiver is positioned on the second drone.

9. The apparatus of claim 1, wherein the processor is further configured to tomographically reconstruct the gas concentration.

10. A method comprising:
moving at least one of a plurality of drones along at least one motion path;
collecting a plurality of gas concentration measurements along a plurality of measurement paths, wherein the plurality of measurement paths are based, at least in part, on the position of at least two of the plurality of drones along the at least one motion path, and wherein at least two of the plurality of measurement paths are not parallel to each other;
reconstructing gas concentration as a function of vertical and horizontal positions across a surface based, at least in part, on the at least two of the plurality of measurement paths that are not parallel to each other and their associated gas concentration measurements; and
determining angles of the plurality of measurement paths between the drones,
wherein the reconstructing of the gas concentration as a function of vertical and horizontal positions across the surface is based, at least in part, on the angles of the plurality of measurement paths between the drones and their associated gas concentration measurements.

11. The method of claim 10, further comprising:
determining wind data corresponding to at least one of the plurality of the gas concentration measurements; and
determining a gas flux through the surface based on the plurality of gas concentration measurements and the wind data.

12. The method of claim 11, wherein the wind data is based on a plurality of wind measurements, the method further comprising collecting the plurality of wind measurements substantially at the same time as collecting the plurality of gas concentration measurements.

13. The method of claim 11, further comprising collecting the plurality of wind measurements at a plurality of heights.

14. The method of claim 10, wherein the surface is downwind of an emission source.

15. The method of claim 10, further comprising:
determining positions of the plurality of drones,
wherein the reconstructing of the gas concentration as a function of horizontal and vertical positions across a surface is based, at least in part, on the positions of the plurality of drones.

16. The method of claim 10, wherein the reconstructing of the gas concentration as a function of horizontal and vertical positions across the surface includes tomographically reconstructing the gas concentration as a function of horizontal and vertical positions across the surface.

17. The method of claim 10, wherein the surface is substantially vertical.

18. The method of claim 10, further comprising:
directing a beam from a source on a first of the at least two of the drones to a reflector on a second of the at least two of the drones;
receiving the beam from the reflector at a receive on the first of the at least two of the drones, and determining one of the plurality of gas concentration measurements based, at least in part, on the received beam.

* * * * *